US011753750B2

(12) United States Patent
Sebastian et al.

(10) Patent No.: US 11,753,750 B2
(45) Date of Patent: Sep. 12, 2023

(54) CONDUCTIVE AEROSOL GENERATING COMPOSITE SUBSTRATE FOR AEROSOL SOURCE MEMBER

(71) Applicant: R.J. Reynolds Tobacco Company, Winston-Salem, NC (US)

(72) Inventors: Andries D. Sebastian, Winston-Salem, NC (US); Stephen B. Sears, Siler City, NC (US); Billy T. Conner, Clemmons, NC (US); Justin William Gage, Greensboro, NC (US); Luis Monsalud, Kernersville, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 1222 days.

(21) Appl. No.: 16/196,958

(22) Filed: Nov. 20, 2018

(65) Prior Publication Data

US 2020/0154784 A1    May 21, 2020

(51) Int. Cl.
*A24F 47/00* (2020.01)
*A24B 15/16* (2020.01)
(Continued)

(52) U.S. Cl.
CPC ........... *D02G 3/441* (2013.01); *A24B 15/167* (2016.11); *H05B 3/56* (2013.01); *D10B 2101/12* (2013.01); *D10B 2101/20* (2013.01); *D10B 2201/20* (2013.01); *D10B 2401/16* (2013.01); *H05B 2203/015* (2013.01); *H05B 2203/021* (2013.01)

(58) Field of Classification Search
None
See application file for complete search history.

(56) References Cited

U.S. PATENT DOCUMENTS

| 2,057,353 A | 10/1936 | Whittemore, Jr. |
| 2,104,266 A | 1/1938 | McCormick |

(Continued)

FOREIGN PATENT DOCUMENTS

| CN | 1541577 A | 11/2004 |
| CN | 2719043 Y | 8/2005 |

(Continued)

OTHER PUBLICATIONS

"Modified Cross-Section Viscose Fibre: Galaxy VY—Trilobl Cellulosic Fibre", <https//web.archive.org/web/20160519070915/http://www.kelheim-fibres.com:80/pdf/TDS_Galaxy_VY_0814.pdf>, pp. 1.

(Continued)

*Primary Examiner* — Shawn Mckinnon
(74) *Attorney, Agent, or Firm* — WOMBLE BOND DICKINSON (US) LLP

(57) ABSTRACT

The present disclosure provides an aerosol source member, a substrate portion, and a method of creating a substrate portion for use in an aerosol source member. In an example implementation, a substrate portion of the present disclosure may comprise a series of overlapping layers of a composite substrate sheet, wherein the composite substrate sheet may comprise a non-woven web at least partially formed from regenerated cellulose fibers, a plurality of conductive threads integrated into the non-woven web, and a coating that includes a fibrous material and an aerosol precursor composition.

45 Claims, 13 Drawing Sheets

(51) Int. Cl.
*D02G 3/44* (2006.01)
*H05B 3/56* (2006.01)
*A24B 15/167* (2020.01)

(56) References Cited

U.S. PATENT DOCUMENTS

| | | | |
|---|---|---|---|
| 3,200,819 A | 8/1965 | Gilbert | |
| 3,860,012 A | 1/1975 | Selke | |
| 3,894,544 A | 7/1975 | Egri | |
| 4,646,764 A | 3/1987 | Young et al. | |
| 4,922,901 A | 5/1990 | Brooks et al. | |
| 5,060,671 A | 10/1991 | Counts et al. | |
| 5,093,894 A | 3/1992 | Deevi et al. | |
| 5,249,586 A | 10/1993 | Morgan et al. | |
| 5,261,424 A | 11/1993 | Sprinkel, Jr. | |
| 5,388,574 A | 2/1995 | Ingebrethsen et al. | |
| 5,396,911 A | 3/1995 | Casey, III et al. | |
| 5,530,225 A | 6/1996 | Hajaligol | |
| 5,571,604 A | 11/1996 | Sprang et al. | |
| 5,687,746 A | 11/1997 | Rose et al. | |
| 5,724,998 A | 3/1998 | Gellatly et al. | |
| 5,726,421 A | 3/1998 | Fleischhauer et al. | |
| 5,819,751 A | 10/1998 | Barnes et al. | |
| 5,865,185 A | 2/1999 | Collins et al. | |
| 5,894,841 A | 4/1999 | Voges | |
| 6,125,853 A | 10/2000 | Susa et al. | |
| 6,155,268 A | 12/2000 | Takeuchi | |
| 7,117,867 B2 | 10/2006 | Cox et al. | |
| 7,647,932 B2 | 1/2010 | Cantrell et al. | |
| 7,832,410 B2 | 11/2010 | Hon | |
| 8,079,371 B2 | 12/2011 | Robinson et al. | |
| 8,314,591 B2 | 11/2012 | Terry et al. | |
| 8,342,184 B2 | 1/2013 | Inagaki et al. | |
| 8,365,742 B2 | 2/2013 | Hon | |
| 8,499,766 B1 | 8/2013 | Newton | |
| 8,839,799 B2 * | 9/2014 | Conner | A24B 15/165 131/194 |
| 9,185,939 B2 | 11/2015 | Jarriault et al. | |
| 9,820,505 B2 | 11/2017 | Gouinguene et al. | |
| 9,833,016 B2 | 12/2017 | Gindrat et al. | |
| 2005/0016550 A1 | 1/2005 | Katase | |
| 2006/0130861 A1 * | 6/2006 | Luan | A24D 3/166 131/335 |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0188490 A1 | 7/2009 | Hon | |
| 2009/0272379 A1 | 11/2009 | Thorens et al. | |
| 2010/0186757 A1 | 7/2010 | Crooks et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0290248 A1 | 12/2011 | Schennum | |
| 2012/0111347 A1 | 5/2012 | Hon | |
| 2012/0260927 A1 | 10/2012 | Liu | |
| 2012/0279512 A1 | 11/2012 | Hon | |
| 2013/0037041 A1 | 2/2013 | Worm et al. | |
| 2013/0056013 A1 | 3/2013 | Terry et al. | |
| 2013/0306084 A1 | 11/2013 | Flick | |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0096781 A1 | 4/2014 | Sears et al. | |
| 2014/0096782 A1 | 4/2014 | Ampolini et al. | |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2014/0305448 A1 | 10/2014 | Zuber et al. | |
| 2015/0059780 A1 | 3/2015 | Davis et al. | |
| 2015/0068541 A1 | 3/2015 | Sears et al. | |
| 2015/0083150 A1 | 3/2015 | Conner et al. | |
| 2015/0101606 A1 | 4/2015 | White | |
| 2015/0107610 A1 | 4/2015 | Metrangolo et al. | |
| 2015/0107611 A1 | 4/2015 | Metrangolo et al. | |
| 2015/0150302 A1 | 6/2015 | Metrangolo et al. | |
| 2015/0181938 A1 | 7/2015 | Metrangolo et al. | |
| 2015/0335070 A1 | 11/2015 | Sears et al. | |
| 2016/0213063 A1 | 7/2016 | Ajithkumar et al. | |
| 2016/0295917 A1 | 10/2016 | Malgat et al. | |
| 2016/0295926 A1 | 10/2016 | Zuber | |
| 2017/0035095 A1 | 2/2017 | Zuchuat et al. | |
| 2017/0042216 A1 | 2/2017 | Gouinguene et al. | |
| 2017/0064996 A1 | 3/2017 | Mironov | |
| 2017/0071250 A1 | 3/2017 | Mironov et al. | |
| 2017/0079325 A1 | 3/2017 | Mironov | |
| 2017/0086508 A1 | 3/2017 | Mironov et al. | |
| 2017/0119049 A1 | 5/2017 | Blandino et al. | |
| 2017/0181465 A1 | 6/2017 | Yang et al. | |
| 2017/0181466 A1 | 6/2017 | Batista | |
| 2017/0258126 A1 | 9/2017 | Klipfel et al. | |
| 2017/0273346 A1 | 9/2017 | Klipfel et al. | |
| 2017/0273347 A1 | 9/2017 | Klipfel et al. | |
| 2017/0273348 A1 | 9/2017 | Klipfel et al. | |

FOREIGN PATENT DOCUMENTS

| | | |
|---|---|---|
| CN | 201379072 Y | 1/2010 |
| EP | 0227422 A2 | 7/1987 |
| EP | 0 295 122 A2 | 12/1988 |
| EP | 0 845 220 A1 | 6/1998 |
| EP | 1 618 803 A1 | 1/2006 |
| GB | 983928 | 2/1965 |
| GB | 2469850 A | 11/2010 |
| RU | 2 233 602 C2 | 8/2004 |
| RU | 2 533 686 C2 | 11/2014 |
| WO | 00/25610 A1 | 5/2000 |
| WO | 2003/034847 A1 | 5/2003 |
| WO | 2004/080216 A1 | 9/2004 |
| WO | 2005/099494 A1 | 10/2005 |
| WO | 2007/131449 A1 | 11/2007 |
| WO | 2017/005705 A1 | 1/2017 |
| WO | 2017/041920 A1 | 3/2017 |
| WO | 2017/051034 A1 | 3/2017 |
| WO | 2017/068092 A1 | 4/2017 |
| WO | 2017/068093 A1 | 4/2017 |
| WO | 2017/068094 A1 | 4/2017 |
| WO | 2017/068100 A1 | 4/2017 |
| WO | 2017/089589 A1 | 6/2017 |
| WO | 2017/153433 A1 | 9/2017 |
| WO | 2017/178394 A1 | 10/2017 |
| WO | 2017/202538 A1 | 11/2017 |
| WO | 2018/178290 A2 | 10/2018 |

OTHER PUBLICATIONS

International Search Report from corresponding International Appl. No. PCT/IB2019/059947, dated Feb. 24, 2020.

* cited by examiner

CONDUCTIVE AEROSOL GENERATING COMPOSITE SUBSTRATE FOR AEROSOL SOURCE MEMBER

FIELD OF THE DISCLOSURE

The present disclosure relates to aerosol source members and uses thereof for yielding tobacco components or other materials in inhalable form. More particularly, the present disclosure relates to substrate materials and aerosol source members containing substrate materials for aerosol delivery devices and systems, such as smoking articles, that utilize electrically-generated heat or combustible carbon-based ignition sources to heat a tobacco or non-tobacco material, preferably without significant combustion, in order to provide an inhalable substance in the form of an aerosol for human consumption.

DESCRIPTION OF RELATED ART

Many smoking articles have been proposed through the years as improvements upon, or alternatives to, smoking products based upon combusting tobacco. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference in their entireties. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference in its entirety. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. Pub. No. 2009/0095311 to Hon; U.S. Pat. Pub. Nos. 2006/0196518, 2009/0126745, and 2009/0188490 to Hon; U.S. Pat. Pub. No. 2009/0272379 to Thorens et al.; U.S. Pat. Pub. Nos. 2009/0260641 and 2009/0260642 to Monsees et al.; U.S. Pat. Pub. Nos. 2008/0149118 and 2010/0024834 to Oglesby et al.; U.S. Pat. Pub. No. 2010/0307518 to Wang; and WO 2010/091593 to Hon, which are incorporated herein by reference in their entireties.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUIFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™, PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd; IQOS™ by Philip Morris International; and GLO™ by British American Tobacco. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

Articles that produce the taste and sensation of smoking by electrically heating tobacco, tobacco derived materials, or other plant derived materials have suffered from inconsistent performance characteristics. For example, some articles have suffered from inconsistent release of flavors or other inhalable materials. Accordingly, it can be desirable to provide a smoking article that can provide the sensations of cigarette, cigar, or pipe smoking, that does so without combusting the substrate material, and that does so with advantageous performance characteristics.

BRIEF SUMMARY

In various implementations, the present disclosure provides a substrate portion for use in an aerosol source member. In one implementation, the substrate portion comprises a series of overlapping layers of a composite substrate sheet, the composite substrate sheet comprising: a non-woven web at least partially formed from regenerated cellulose fibers, a plurality of conductive threads integrated into the non-woven web, and a coating that includes a fibrous material and an aerosol precursor composition. In some implementations, the regenerated cellulose fibers may have a multi-lobal cross-section. In some implementations, the fibrous material may comprise a milled tobacco material. In some implementations, the coating may further include one or more of a binder material, a burn retardant material, and a flavorant. In some implementations, the non-woven web may be configured to contain the aerosol precursor composition in a loading in excess of 40%. In some implementations, the non-woven web may be configured to contain the aerosol precursor composition in a loading from at least 10% to in excess of 50%. In some implementations, the plurality of conductive threads may be arranged in a substantially linear and parallel pattern. In some implementations, the plurality of conductive threads may have a substantially random arrangement. In some implementations, the plurality of conductive threads may be constructed of or more of an aluminum material, a stainless steel material, a copper material, a carbon material, and a graphite material. In some implementations, the plurality of conductive threads may be integrated into non-woven web via stitching. In some implementations, the plurality of conductive threads may be integrated into non-woven web via tailored fiber placement (TFP). In some implementations, the plurality of conductive threads may be integrated into the non-woven web via stitch bonding. In some implementations, the composite substrate sheet may comprise two or more layers stitch bonded together.

In some implementations, the series of overlapping layers of the composite substrate sheet may be wrapped on its outside with a cover layer. In some implementations, the cover layer may comprise a cast sheet. In some implementations, the cover layer may comprise a non-woven web at least partially formed from regenerated cellulose fibers. In some implementations, the series of overlapping layers of the composite substrate sheet and the cover layer may be wrapped on the outside thereof with a second cover layer comprising a metal foil. In some implementations, the series of overlapping layers of the composite substrate sheet, the cover layer, and the second cover layer may be wrapped on the outside thereof with a third cover layer comprising a paper material. Some implementations may further comprise a binder material, an aerosol precursor composition, and a burn retardant material.

In various implementations, the present disclosure also provides an aerosol source member. In one implementation, the aerosol source member comprises a substrate portion comprising: a series of overlapping layers of a composite substrate sheet, the composite substrate sheet comprising: a non-woven web at least partially formed from regenerated cellulose fibers, a plurality of conductive threads integrated into the non-woven web, and a coating that includes a fibrous material and an aerosol precursor composition. The substrate portion is formed in a substantially cylindrical shape, and a cover layer is disposed proximate an outside surface of the substrate portion. In some implementations, the regenerated cellulose fibers of the substrate portion may have a multi-lobal cross-section. In some implementations, the fibrous material of the substrate portion may comprise a milled tobacco material. In some implementations, the coating of the substrate portion may further include one or more of a binder material, a burn retardant material, and a flavorant. In some implementations, the cover layer may comprise a cast sheet. In some implementations, the cover layer may comprise a non-woven web at least partially formed from regenerated cellulose fibers.

Some implementations may further comprise a second cover layer disposed proximate an outer surface of the cover layer, the second cover layer comprising a metal foil. Some implementations may further comprise a third cover layer disposed proximate an outer surface of the second cover layer, wherein the third cover layer comprises a paper material. In some implementations, the non-woven web of the substrate portion may be configured to contain the aerosol precursor composition at a loading in excess of 40%. In some implementations, the non-woven web of the substrate portion may be configured to contain the aerosol precursor composition in a loading from at least 10% to in excess of 50%. In some implementations, the plurality of conductive threads of the substrate portion may be arranged in a substantially linear and parallel pattern. In some implementations, the plurality of conductive threads may have a substantially random arrangement. In some implementations, the plurality of conductive threads of the substrate portion may be constructed of or more of an aluminum material, a stainless steel material, a copper material, a carbon material, a graphite material. In some implementations, the plurality of conductive threads of the substrate portion may be integrated into non-woven web via stitching. In some implementations, the plurality of conductive threads of the substrate portion may be integrated into non-woven web via tailored fiber placement (TFP). In some implementations, the plurality of conductive threads may be integrated into the non-woven web via stitch bonding. In some implementations, the composite substrate sheet may comprise two or more layers stitch bonded together.

In various implementations, the present disclosure also provides a method of creating a substrate portion for use in an aerosol source member. In one implementation, the method comprises creating a composite substrate sheet by: forming a non-woven web using regenerated cellulose fibers, integrating a plurality of conductive threads into the non-woven web, and coating the non-woven web and integrated conductive threads with a coating that includes a fibrous material and an aerosol precursor composition, and overlapping a plurality of layers of the composite substrate sheet to create a series of overlapping layers of the composite substrate sheet. In some implementations, the regenerated cellulose fibers may have a multi-lobal cross-section. In some implementations, the fibrous material may comprise a milled tobacco material. In some implementations, the coating may further include one or more of a binder material, a burn retardant material, and a flavorant. In some implementations, the non-woven web may be configured to contain the aerosol precursor composition in a loading in excess of 40%. In some implementations, the non-woven web may be configured to contain the aerosol precursor composition in a loading from at least 10% to in excess of 50%. In some implementations, the step of integrating the plurality of conductive threads into the non-woven web may comprise integrating the plurality of conductive threads so that they are arranged in a substantially linear and parallel pattern. In some implementations, the plurality of conductive threads may have a substantially random arrangement. In some implementations, the plurality of conductive threads may be constructed of or more of an aluminum material, a stainless steel material, a copper material, a carbon material, and a graphite material. In some implementations, the step of integrating the plurality of conductive threads into the non-woven web may comprise stitching the plurality of conductive threads into the non-woven web. In some implementations, the step of integrating the plurality of conductive threads into the non-woven web may comprise tailored fiber placement (TFP). In some implementations, the plurality of conductive threads may be integrated into the non-woven web via stitch bonding. In some implementations, the composite substrate sheet may comprise two or more layers stitch bonded together.

Some implementations may further comprise wrapping the series of overlapping layers of the composite substrate sheet about an outer surface thereof with a cover layer. In some implementations, the cover layer may comprise a cast sheet. In some implementations, the cover layer may comprise a non-woven web at least partially formed from regenerated cellulose fibers. Some implementations may further comprise wrapping the series of overlapping layers of the composite substrate sheet and the cover layer about an outer surface thereof with a second cover layer comprising a metal foil. Some implementations may further comprise wrapping the series of overlapping layers of the composite substrate sheet, the cover layer, and the second cover layer about an outer surface thereof with a third cover layer comprising a paper material.

These and other features, aspects, and advantages of the disclosure will be apparent from a reading of the following detailed description together with the accompanying drawings, which are briefly described below.

BRIEF DESCRIPTION OF THE FIGURES

Figure 1:
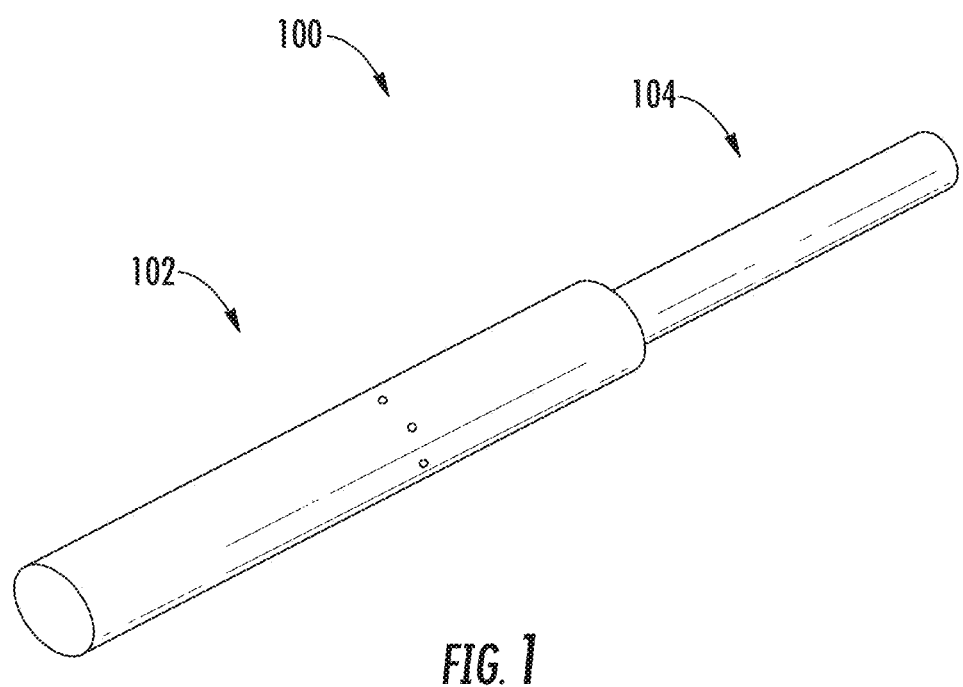
Figure 2:
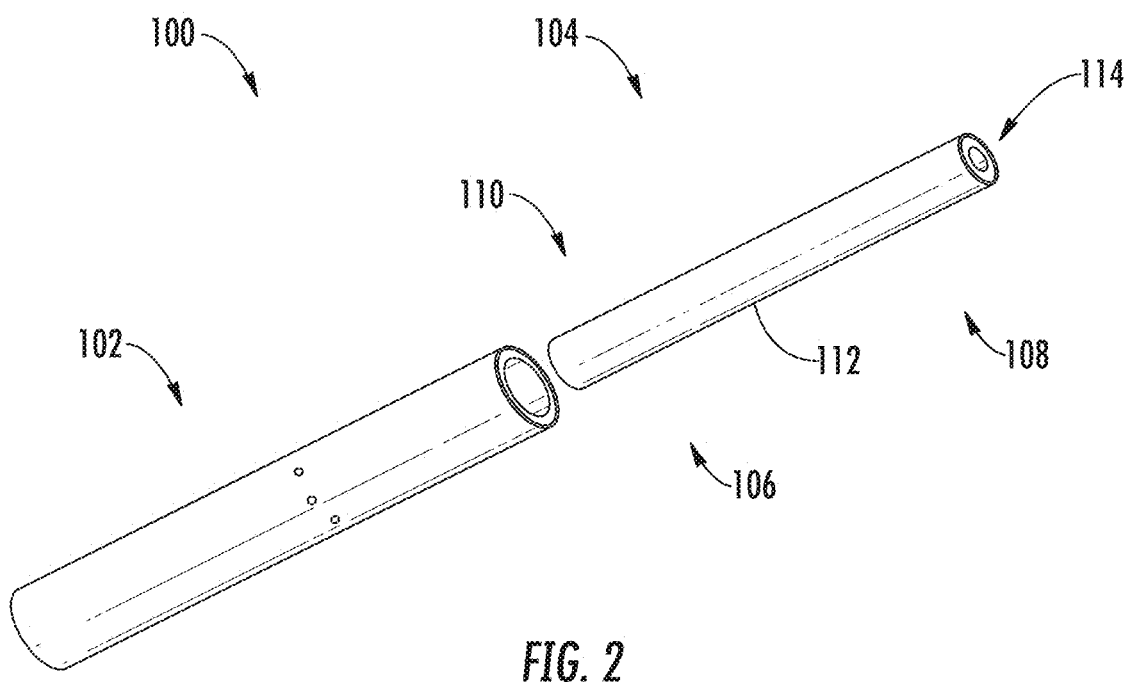
Figure 3:
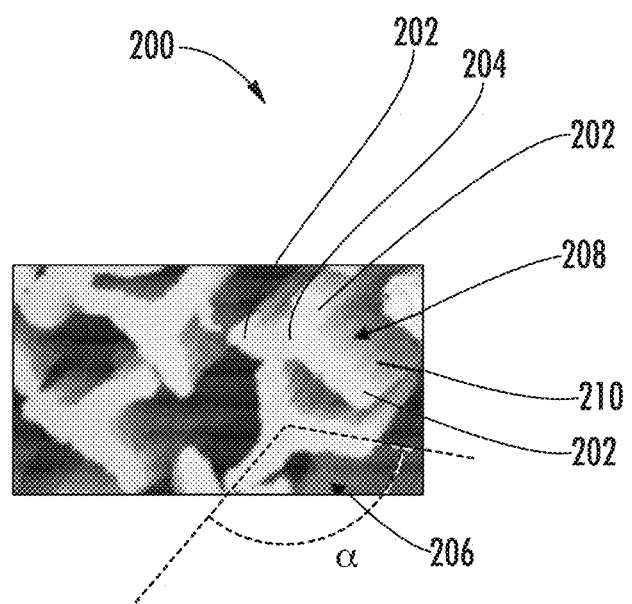
Figure 4:
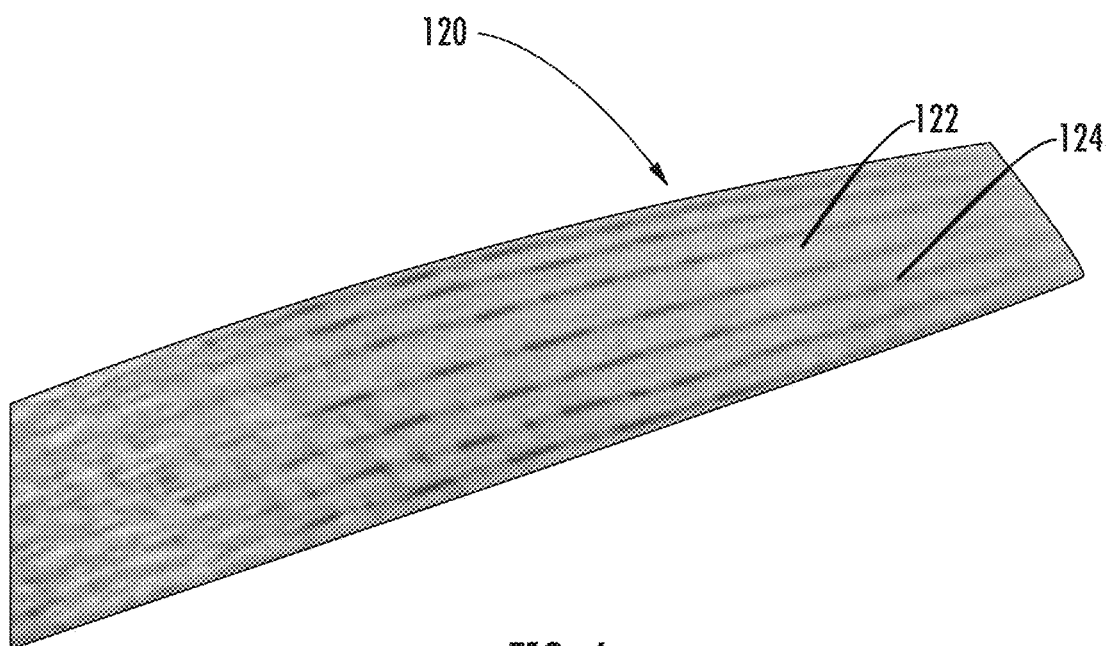
Figure 5:
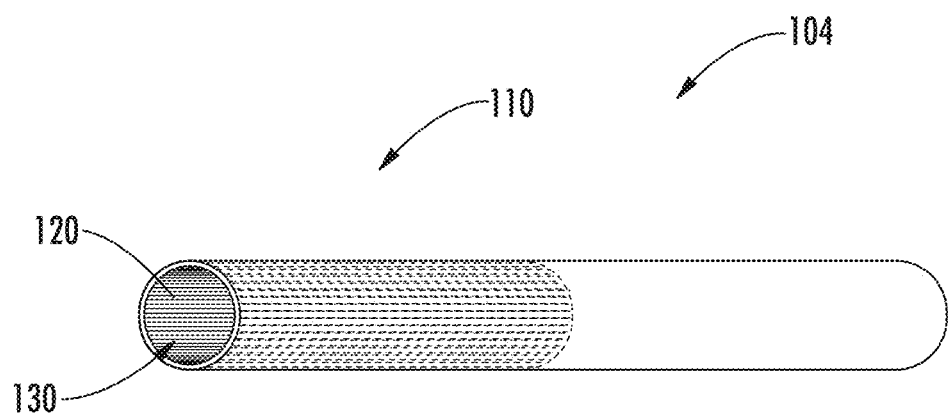
Figure 6:
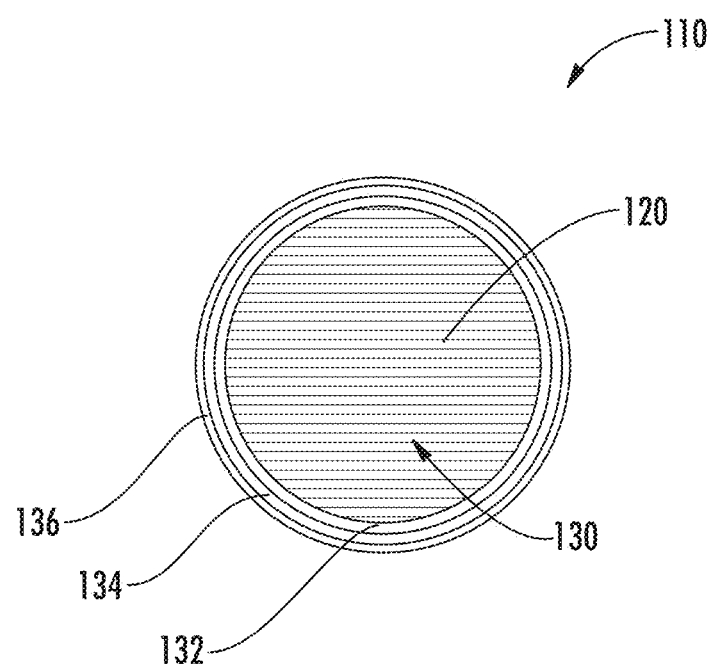
Figure 7:
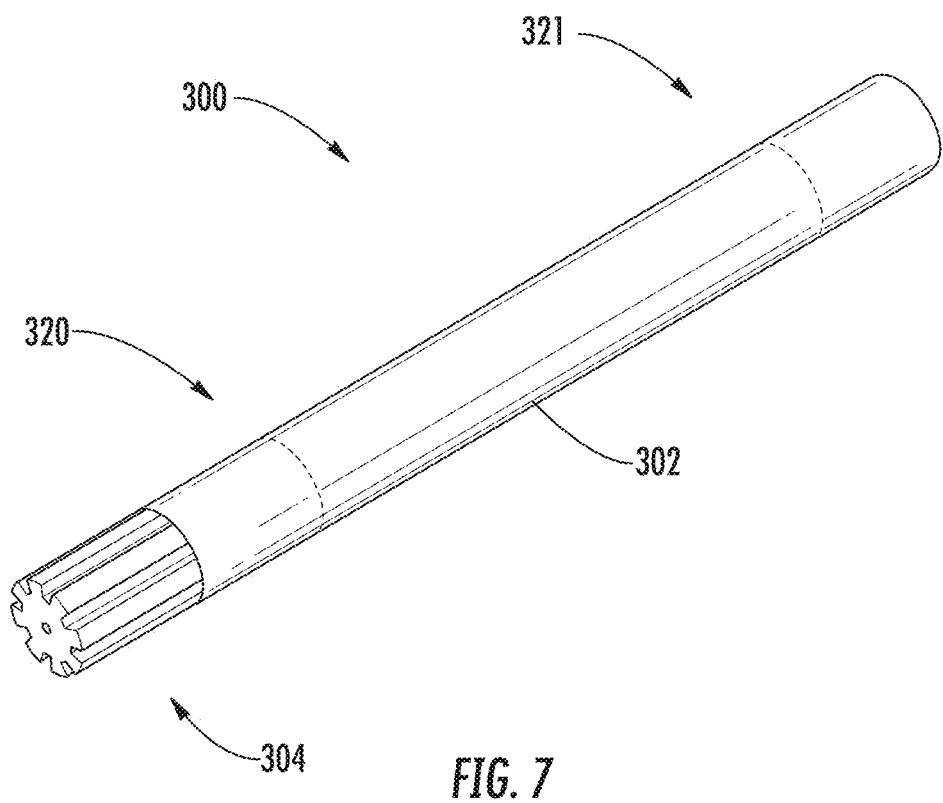
Figure 8:
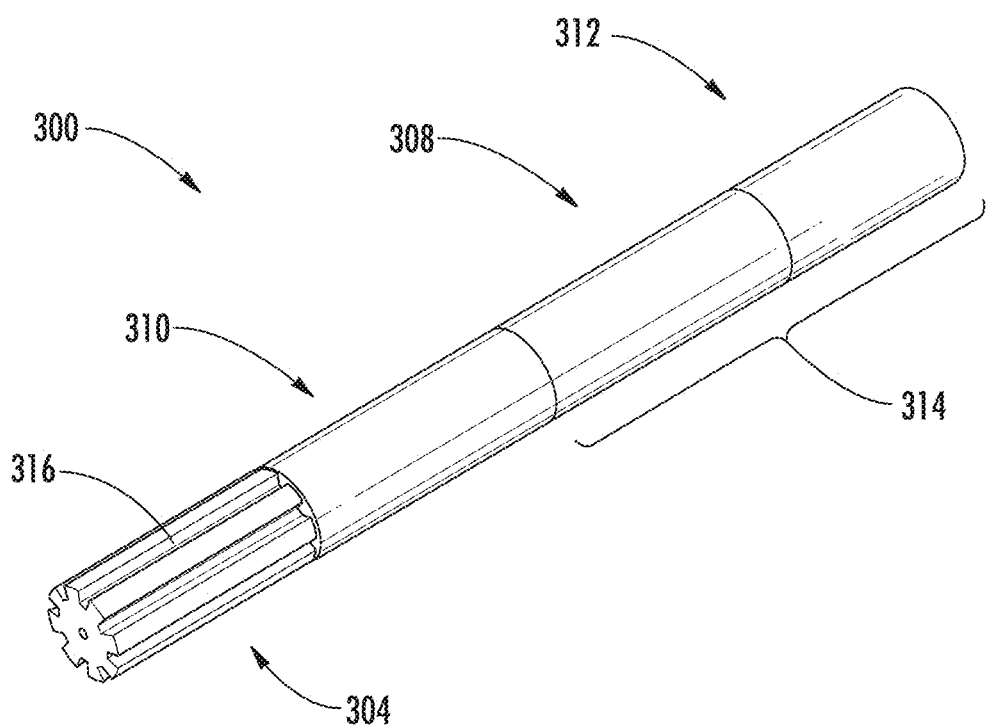
Figure 9:
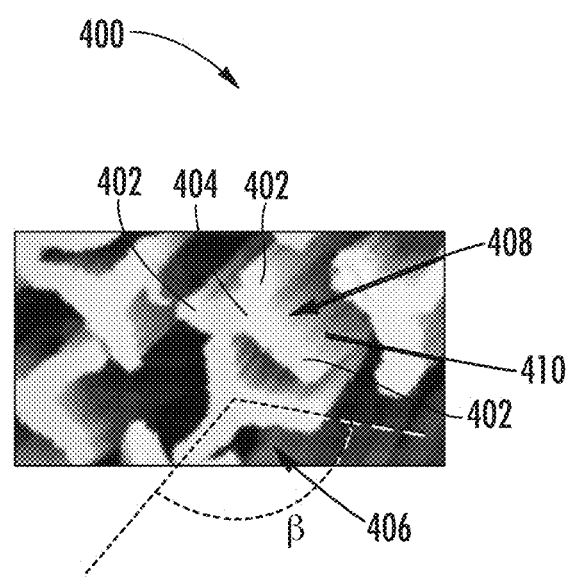
Figure 10:
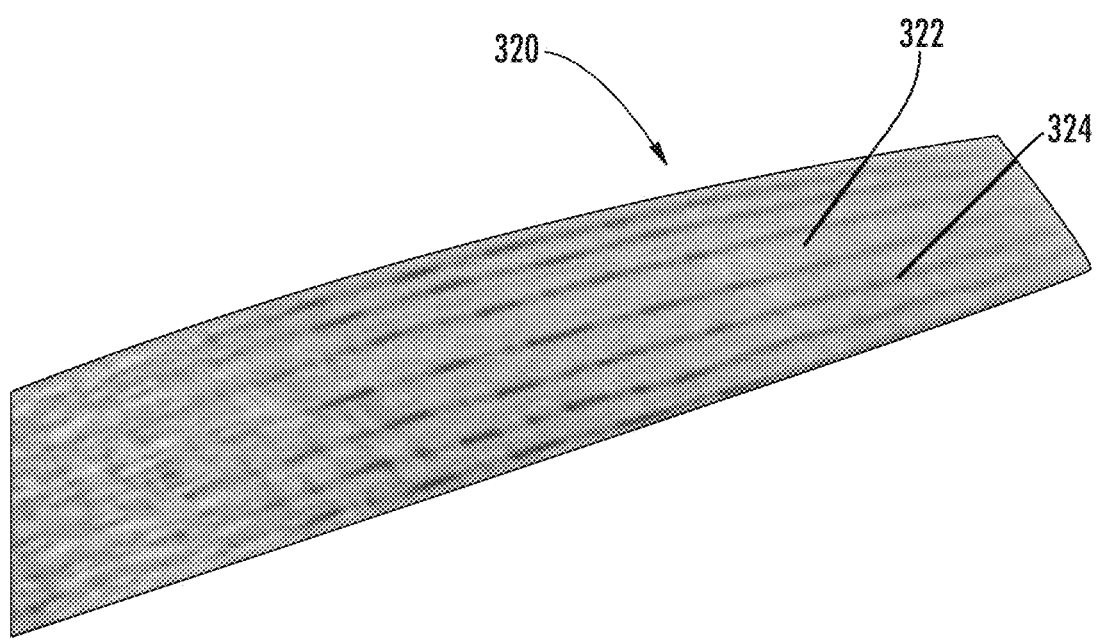
Figure 11:
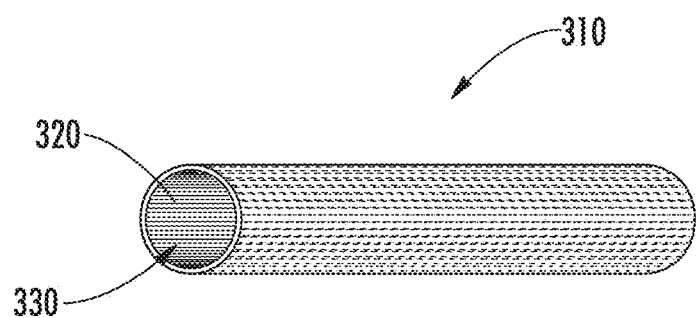
Figure 12:
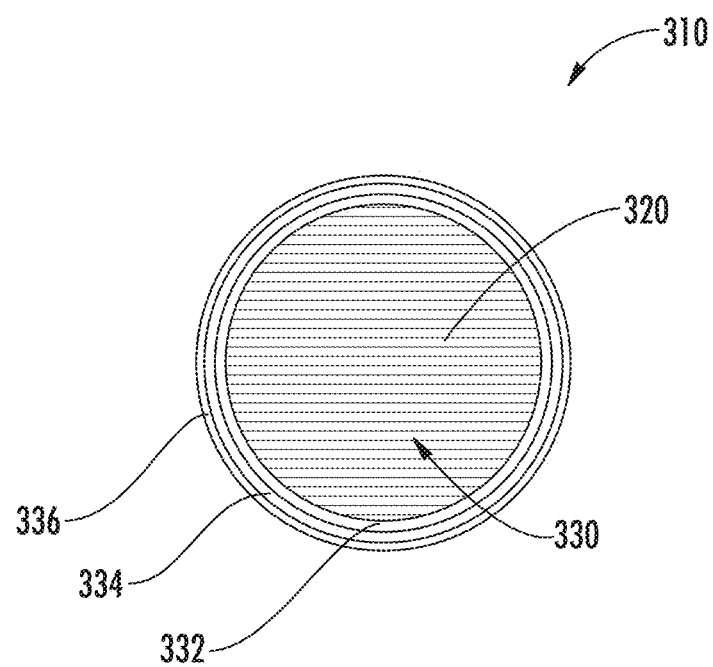
Figure 13:
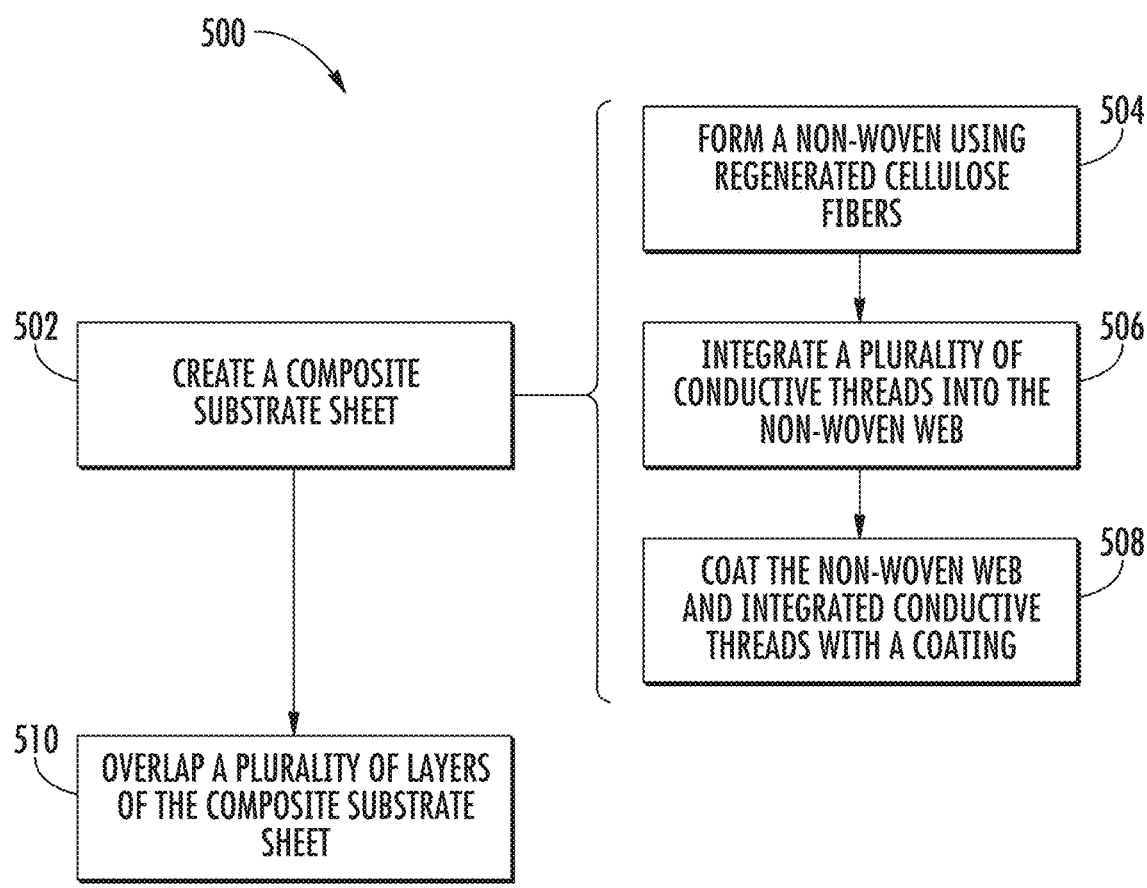

Having thus described aspects of the disclosure in the foregoing general terms, reference will now be made to the accompanying drawings, which are not necessarily drawn to scale, and wherein:

FIG. 1 illustrates a perspective view of an aerosol delivery device comprising a control body and an aerosol source member, wherein the aerosol source member and the control body are coupled to one another, according to an example implementation of the present disclosure;

FIG. 2 illustrates a perspective view of the aerosol delivery device of FIG. 1 wherein the aerosol source member and the control body are decoupled from one another, according to an example implementation of the present disclosure;

FIG. 3 illustrates a schematic cross-section drawing of fibers of a composite substrate sheet, according to an example implementation of the present disclosure;

FIG. 4 illustrates a schematic drawing of a non-woven web with integrated conductive threads, according to an example implementation of the present disclosure;

FIG. 5 illustrates a perspective schematic view of an aerosol source member, according to an example implementation of the disclosure;

FIG. 6 illustrates a schematic cross-section drawing of a substrate portion of an aerosol source member, according to an example implementation of the present disclosure;

FIG. 7 illustrates a perspective view of an aerosol source member, according to an example implementation of the present disclosure;

FIG. 8 illustrates a perspective view of the aerosol source member of FIG. 7 with an outer wrap removed, according to one implementation of the present disclosure;

FIG. 9 illustrates a schematic cross-section drawing of fibers of a composite substrate sheet, according to an example implementation of the present disclosure;

FIG. 10 illustrates a schematic drawing of a non-woven web with integrated conductive threads, according to an example implementation of the present disclosure;

FIG. 11 illustrates a perspective schematic view of a substrate portion of an aerosol delivery device, according to an example implementation of the disclosure;

FIG. 12 illustrates a schematic cross-section drawing of a substrate portion of an aerosol delivery device, according to an example implementation of the present disclosure; and FIG. 13 illustrates various operations in a method of manufacturing a substrate portion for use with an aerosol delivery device, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol generating substrates for use in an aerosol source members and aerosol source members for use with aerosol delivery devices. Some implementations of aerosol source members according to the present disclosure use electrical energy to heat a material to form an inhalable substance (e.g., electrically heated tobacco products). Other implementations of aerosol source members according to the present disclosure use an ignitable heat source to heat a material (preferably without combusting the material to any significant degree) to form an inhalable substance (e.g., carbon heated tobacco products). Preferably, the material is heated without combusting the material to any significant degree. Components of such systems have the form of articles that are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices and/or aerosol source members may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices and/or aerosol source members such as so-called "e-cigarettes" or "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices and/or aerosol source members of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some implementations, the terms "vapor" and "aerosol" may be interchangeable. Thus, for simplicity, the terms "vapor" and "aerosol" as used to describe aspects of the disclosure are understood to be interchangeable unless stated otherwise.

In some implementations, aerosol delivery devices of the present disclosure may comprise some combination of a power source (e.g., an electrical power source), at least one control component (e.g., means for actuating, controlling, regulating and ceasing power for heat generation, such as by controlling electrical current flow from the power source to other components of the article—e.g., a microprocessor, individually or as part of a microcontroller), a heating member (e.g., an electrical resistance heating element or other component and/or an inductive coil or other associated components and/or one or more radiant heating elements), and an aerosol source member that includes a substrate portion capable of yielding an aerosol upon application of sufficient heat. In various implementations, a number of these components may be provided within an outer body or shell, which, in some implementations, may be referred to as a housing. The overall design of the outer body or shell may vary, and the format or configuration of the outer body that may define the overall size and shape of the aerosol delivery device may vary. Although other configurations are possible, in some implementations an elongated body resembling the shape of a cigarette or cigar may be a formed from a single, unitary housing or the elongated housing can be formed of two or more separable bodies. For example, an aerosol delivery device may comprise an elongated shell or body that may be substantially tubular in shape and, as such, resemble the shape of a conventional cigarette or cigar. In one example, all of the components of the aerosol delivery device are contained within one housing or body. In other implementations, an aerosol delivery device may comprise two or more housings that are joined and are separable. For example, an aerosol delivery device may possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing aerosol source member).

In other implementations, aerosol source members of the present disclosure may generally include an ignitable heat source configured to heat a substrate material. The substrate material and/or at least a portion of the heat source may be covered in an outer wrap, or wrapping, a casing, a component, a module, a member, or the like. The overall design of the enclosure is variable, and the format or configuration of the enclosure that defines the overall size and shape of the aerosol source member is also variable. Although other configurations are possible, it may be desirable, in some aspects, that the overall design, size, and/or shape of these implementations resemble that of a conventional cigarette or cigar. In various aspects, the heat source may be capable of generating heat to aerosolize a substrate material that comprises, for example, a substrate material associated with an aerosol precursor composition, an extruded structure and/or substrate, tobacco and/or a tobacco related material, such as a material that is found naturally in tobacco that is isolated directly from the tobacco or synthetically prepared, in a solid or liquid form (e.g., beads, sheets, shreds, a wrap), or the like.

More specific formats, configurations and arrangements of various substrate materials, aerosol source members, and components within aerosol delivery devices of the present disclosure will be evident in light of the further disclosure provided hereinafter. Additionally, the selection of various aerosol delivery device components may be appreciated upon consideration of the commercially available electronic aerosol delivery devices. Further, the arrangement of the components within the aerosol delivery device may also be appreciated upon consideration of the commercially available electronic aerosol delivery devices.

In this regard, FIG. 1 illustrates an aerosol delivery device 100 according to an example implementation of the present disclosure. The aerosol delivery device 100 may include a control body 102 and an aerosol source member 104. In various implementations, the aerosol source member 104 and the control body 102 may be permanently or detachably aligned in a functioning relationship. In this regard, FIG. 1 illustrates the aerosol delivery device 100 in a coupled configuration, whereas FIG. 2 illustrates the aerosol delivery device 100 in a decoupled configuration. Various mechanisms may connect the aerosol source member 104 to the control body 102 to result in a threaded engagement, a press-fit engagement, an interference fit, a sliding fit, a magnetic engagement, or the like.

In various implementations, the aerosol delivery device 100 according to the present disclosure may have a variety of overall shapes, including, but not limited to an overall shape that may be defined as being substantially rod-like or substantially tubular shaped or substantially cylindrically shaped. In the implementations of FIGS. 1-2, the device 100 has a substantially round cross-section; however, other cross-sectional shapes (e.g., oval, square, triangle, etc.) also are encompassed by the present disclosure. For example, in some implementations one or both of the control body 102 or the aerosol source member 104 (and/or any subcomponents) may have a substantially rectangular shape, such as a substantially rectangular cuboid shape (e.g., similar to a USB flash drive). In other implementations, one or both of the control body 102 or the aerosol source member 104 (and/or any subcomponents) may have other hand-held shapes. For example, in some implementations the control body 102 may have a small box shape, various pod mod shapes, or a fob-shape. Thus, such language that is descriptive of the physical shape of the article may also be applied to the individual components thereof, including the control body 102 and the aerosol source member 104.

Alignment of the components within the aerosol delivery device of the present disclosure may vary across various implementations. In some implementations, the substrate portion may be positioned proximate a heating member so as to maximize aerosol delivery to the user. Other configurations, however, are not excluded. Generally, the heating member may be positioned sufficiently near the substrate portion so that heat from the heating member can volatilize the substrate portion (as well as, in some implementations, one or more flavorants, medicaments, or the like that may likewise be provided for delivery to a user) and form an aerosol for delivery to the user. When the heating member heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device 100 of various implementations may incorporate a battery and/or other electrical power source to provide current flow sufficient to provide various functionalities to the aerosol delivery device, such as powering of the heating member, powering of control systems, powering of indicators, and the like. As will be discussed in more detail below, the power source may take on various implementations. Preferably, the power source may be able to deliver sufficient power to rapidly activate the heating member to provide for aerosol formation and power the aerosol delivery device through use for a desired duration of time. In some implementations, the power source is sized to fit conveniently within the aerosol delivery device so that the aerosol delivery device can be easily handled. Examples of useful power sources include lithium-ion batteries that are preferably rechargeable (e.g., a rechargeable lithium-manganese dioxide battery). In particular, lithium polymer batteries can be used as such batteries can provide increased safety. Other types of batteries—e.g., N50-AAA CADNICA nickel-cadmium cells—may also be used. Additionally, a preferred power source is of a sufficiently light weight to not detract from a desirable smoking experience. Some examples of possible power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties.

In specific implementations, one or both of the control body 102 and the aerosol source member 104 may be referred to as being disposable or as being reusable. For example, the control body 102 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 104 may comprise a single-use device. A single use component for use with a control body is disclosed in U.S. Pat. No. 8,910,639 to Chang et al., which is incorporated herein by reference in its entirety.

In further implementations, the power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor.

Further components may be utilized in the aerosol delivery device of the present disclosure. For example, the aerosol delivery device may include a flow sensor that is sensitive either to pressure changes or air flow changes as the consumer draws on the article (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference is also made to the control schemes described in U.S. Pat. No. 9,423,152 to Ampolini et al., which is incorporated herein by reference in its entirety.

In another example, an aerosol delivery device may comprise a first conductive surface configured to contact a first body part of a user holding the device, and a second conductive surface, conductively isolated from the first conductive surface, configured to contact a second body part of the user. As such, when the aerosol delivery device detects a change in conductivity between the first conductive surface and the second conductive surface, a vaporizer is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

In addition, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

Referring to FIG. 2, in the depicted implementation, the aerosol source member 104 comprises a heated end 106, which is configured to be inserted into the control body 102, and a mouth end 108, upon which a user draws to create the aerosol. At least a portion of the heated end 106 may include a substrate portion 110. As will be discussed in more detail below, in various implementations the substrate portion 110 may comprise a series of overlapping layers of a composite substrate sheet that comprises a non-woven web at least partially formed from regenerated cellulose fibers. In various implementations, the aerosol source member 104, or a portion thereof, may be wrapped in an exterior overwrap material 112. In various implementations, the mouth end 108 of the aerosol source member 104 may include a filter 114, which may, for example, be made of a cellulose acetate or polypropylene material. The filter 114 may additionally or alternatively contain strands of tobacco containing material, such as described in U.S. Pat. No. 5,025,814 to Raker et al., which is incorporated herein by reference in its entirety. In various implementations, the filter 114 may increase the structural integrity of the mouth end of the aerosol source member, and/or provide filtering capacity, if desired, and/or provide resistance to draw. In some implementations, the filter may comprise discrete segments. For example, some implementations may include a segment providing filtering, a segment providing draw resistance, a hollow segment providing a space for the aerosol to cool, a segment providing increased structural integrity, other filter segments, and any one or any combination of the above.

In some implementations, the material of the exterior overwrap 112 may comprise a material that resists transfer of heat, which may include a paper or other fibrous material, such as a cellulose material. The exterior overwrap material may also include at least one filler material imbedded or dispersed within the fibrous material. In various implementations, the filler material may have the form of water insoluble particles. Additionally, the filler material may incorporate inorganic components. In various implementations, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the exterior overwrap at the mouth end 108 of the aerosol source member may function to simply separate the substrate portion 110 from the mouth of a consumer or to provide space for positioning of a filter material, as described below, or to affect draw on the article or to affect flow characteristics of the vapor or aerosol leaving the device during draw. Further discussions relating to the configurations for exterior overwrap materials that may be used with the present disclosure may be found in U.S. Pat. No. 9,078,473 to Worm et al., which is incorporated herein by reference in its entirety.

In various implementations, other components may exist between the substrate portion 110 and the mouth end 108 of the aerosol source member 104. For example, in some implementations one or any combination of the following may be positioned between the substrate portion 110 and the mouth end 108 of the aerosol source member 104: an air gap; a hollow tube structure; phase change materials for cooling air; flavor releasing media; ion exchange fibers capable of selective chemical adsorption; aerogel particles as filter medium; and other suitable materials. Some examples of possible phase change materials include, but are limited to, salts, such as $AgNO_3$, $AlCl_3$, $TaCl_3$, $InCl_3$, $SnCl_2$, $AlI_3$, and $TiI_4$; metals and metal alloys such as selenium, tin, indium, tin-zinc, indium-zinc, or indium-bismuth; and organic compounds such as D-mannitol, succinic acid, p-nitrobenzoic acid, hydroquinone and adipic acid. Other examples are described in U.S. Pat. No. 8,430,106 to Potter et al., which is incorporated herein by reference in its entirety.

As will be discussed in more detail below, the present disclosure is configured for use with a conductive and/or inductive heat source to heat a substrate material to form an aerosol. In various implementations, a conductive heat source may comprise a heating assembly that comprises a resistive heating member. Resistive heating members may be configured to produce heat when an electrical current is directed therethrough. Electrically conductive materials useful as resistive heating members may be those having low mass, low density, and moderate resistivity and that are thermally stable at the temperatures experienced during use. Useful heating members heat and cool rapidly, and thus provide for the efficient use of energy. Rapid heating of the member may be beneficial to provide almost immediate volatilization of an aerosol precursor material in proximity thereto. Rapid cooling prevents substantial volatilization (and hence waste) of the aerosol precursor material during periods when aerosol formation is not desired. Such heating members may also permit relatively precise control of the temperature range experienced by the aerosol precursor material, especially when time based current control is employed. Useful electrically conductive materials are preferably chemically non-reactive with the materials being heated (e.g., aerosol precursor materials and other inhalable substance materials) so as not to adversely affect the flavor or content of the aerosol or vapor that is produced. Some example, non-limiting, materials that may be used as the electrically conductive material include carbon, graphite, carbon/graphite composites, metals, ceramics such as metallic and non-metallic carbides, nitrides, oxides, silicides, inter-metallic compounds, cermets, metal alloys, and metal foils. In particular, refractory materials may be useful. Various, different materials can be mixed to achieve the desired properties of resistivity, mass, and thermal conductivity. In specific implementations, metals that can be utilized include, for example, nickel, chromium, alloys of nickel and chromium (e.g., nichrome), and steel. Materials that can be useful for providing resistive heating are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

In various implementations, a heating member may be provided in a variety of forms, such as in the form of a foil, a foam, a mesh, a hollow ball, a half ball, discs, spirals, fibers, wires, films, yarns, strips, ribbons, or cylinders. Such heating members often comprise a metal material and are configured to produce heat as a result of the electrical resistance associated with passing an electrical current therethrough. Such resistive heating members may be positioned in proximity to, and/or in direct contact with, the substrate portion. For example, in one implementation, a heating member may comprise a cylinder or other heating device located in the control body 102, wherein the cylinder is constructed of one or more conductive materials, including, but not limited to, copper, aluminum, platinum, gold, silver, iron, steel, brass, bronze, carbon (e.g., graphite), or any combination thereof. In various implementations, the heating member may also be coated with any of these or other conductive materials. The heating member may be located proximate an engagement end of the control body 102, and may be configured to substantially surround a portion of the heated end 106 of the aerosol source member 104 that includes the substrate portion 110. In such a manner, the heating member may be located proximate the substrate portion 110 of the aerosol source member 104 when the aerosol source member is inserted into the control body 102. In other examples, at least a portion of a heating member may penetrate at least a portion of an aerosol source member (such as, for example, one or more prongs and/or spikes that penetrate an aerosol source member), when the aerosol source member is inserted into the control body.

As will be discussed in more detail below, in various implementations, a plurality of thermally and/or electrically conductive threads may be integrated into a substrate sheet to create a composite substrate sheet. In various implementations, the composite substrate sheet may be used to create a substrate portion of an aerosol source member. As such, in various implementations, when the heating member is heated, the thermally and electrically conductive threads may increase heat conduction within the substrate portion. Although in some implementations the heating member may comprise a cylinder, it should be noted that in other implementations, the heating member may take a variety of forms and, in some implementations, may make direct contact with and/or penetrate the substrate portion. Some examples of heating members that may be applicable to the present disclosure can be found in U.S. patent application Ser. No. 15/916,834, filed on Mar. 9, 2018, and titled Electronically Heated Heat-Not-Burn Smoking Article, which is incorporated herein by reference in its entirety.

As described above, in addition to being configured for use with a conductive heat source, the present disclosure may also be configured for use with an inductive heat source to heat a substrate portion to form an aerosol. In various implementations, an inductive heat source may comprise a resonant transformer, which may comprise a resonant transmitter and a resonant receiver (e.g., a susceptor). In some implementations, the resonant transmitter and the resonant receiver may be located in the control body 102. In other implementations, the resonant receiver, or a portion thereof, may be located in the aerosol source member 104. For example, in some implementations, the control body 102 may include a resonant transmitter, which, for example, may comprise a foil material, a coil, a cylinder, or other structure configured to generate an oscillating magnetic field, and a resonant receiver, which may comprise one or more prongs that extend into the substrate portion or are surrounded by the substrate portion.

In other implementations, a resonant transmitter may comprise a helical coil configured to circumscribe a cavity into which an aerosol source member, and in particular, a substrate portion of an aerosol source member, is received. In some implementations, the helical coil may be located between an outer wall of the device and the receiving cavity. In one implementation, the coil winds may have a circular cross section shape; however, in other implementations, the coil winds may have a variety of other cross section shapes, including, but not limited to, oval shaped, rectangular shaped, L-shaped, T-shaped, triangular shaped, and combinations thereof. In another implementation, a pin may extend into a portion of the receiving cavity, wherein the pin may comprise the resonant transmitter, such as by including a coil structure around or within the pin. In various implementations, an aerosol source member may be received in the receiving cavity wherein one or more components of the aerosol source member may serve as the resonant receiver. Other possible resonant transformer components, including resonant transmitters and resonant receivers, are described in U.S. patent application Ser. No. 15/799,365, filed on Oct. 31, 2017, and titled Induction Heated Aerosol Delivery Device, which is incorporated herein by reference in its entirety.

As noted above, in various implementations the substrate portion 110 may comprise a series of overlapping layers of a composite substrate sheet that comprises a non-woven web at least partially formed from regenerated cellulose fibers. As a non-limiting example, a suitable regenerated cellulose fiber may be a viscose fiber prepared from any variety of cellulose-containing materials, such as wood (e.g., eucalyptus trees), grasses (e.g., bamboo), cotton, and other plant-based materials. In addition to the type of material used to form the fibers, substrate sheets as disclosed herein may exhibit desirable properties as least in part due to the physical structure of the fiber. It is common for fibers (particularly extruded fibers) to be solid and have a substantially round cross-section. While fibers of such construction may also be included in the present substrate sheets (e.g., as a blend), it can be particularly useful for the substrate sheets to include fibers having a multi-lobal cross-section. For example, the present substrate sheets may comprise multi-lobal fibers in an amount of about 25% or more, about 50% or more, about 60% or more, about 75% or more, about 90% or more, or about 99% or more by weight based on the total weight of fibers present in the substrate.

It should be understood that the foregoing values will have an inherent maximum of 100% by weight—e.g., wherein all fibers used in forming the substrate sheet are multi-lobal fibers. In some implementations, the multi-lobal fibers may comprise about 25% to about 100%, about 50% to about 100%, or about 90% to about 100% by weight of the substrate sheet, based on the total weight of fibers present in the substrate sheet. It should be understood that the terms "multi-lobal fiber" and "fiber having a multi-lobal cross-section" are meant to be interchangeable. In some implementations, a multi-lobal fiber can be a fiber that, in cross-section, includes a common base or hub (typically at about a central portion of the cross-section of the fiber) with at least three lobes or spokes extending therefrom. A multi-lobal fiber may further be defined as a fiber having three or more extensions such that at least one set of adjacent extensions form an angle of less than 180 degrees and thereby define one or more channels extending longitudinally along the fiber. Non-limiting examples of multi-lobal fibers are shown in FIG. 3.

As seen in FIG. 3, a multi-lobal fiber 200 includes a plurality of lobes 202 extending from a central hub 204, with adjacent lobes having an angle $\alpha$ that is less than 180 degrees so as to form a channel 206 between the adjacent lobes. The lobes of a multi-lobal fiber can have a variety of shapes. For example, in some implementations the plurality of lobes may be substantially rounded while still forming a plurality of channels between adjacent lobes. In another implementation, a multi-lobal fiber may have a cross-section that is substantially elongated so as to allow for a greater number of lobes and thus a greater number of channels between the adjacent lobes. The number of lobes can vary and can be for example, 3 to 30, 3 to 20, or 3 to 10. Likewise, the spacing between lobes and the size of the lobes in the same fiber can vary. The multi-lobal fibers preferably can include surface features that can further improve the liquid handling properties thereof. As seen in FIG. 3, the plurality of lobes 202 include outer surfaces 208 that have a plurality of striations 210 that form micro- or nano-channels that can further the liquid retention and/or liquid transfer abilities of the fibers. A specific example of a multi-lobal fiber that is also striated and that can be particularly useful according to the present disclosure is fibers sold under the brand name GALAXY® from Kelheim Fibres.

A substrate sheet according to the present disclosure can be formed of a single layer of nonwoven fibers. A layer of fibers can be formed by any suitable method, such as wet-laid methods and dry-laid methods (e.g., carding or air-laid methods). Preferably, the fibers utilized in forming the substrates are staple fibers. If desired, a binder may be used, such as binders that typically may be used with cellulose esters. A binder is understood to be a material that imparts a cohesive effect to the fibers used in forming the disclosed reservoirs. For example, the binder can be a material that partially solubilizes the fibers such that the fibers bind to each other or to further fibrous materials included in the non-woven reservoir. Some example binders that can be used include polyvinyl acetate (PVA) binders, starch, and triacetin. In some implementations, cohesiveness may be provided through alternate means, such as through needle punching or other mechanical processes for intertwining the fibers (e.g., hydro-entanglement). A substrate sheet thus can be defined by the actual physical structure of being a needle-punched substrate in that the fibers are intertwined in a manner that would not be present prior to undertaking a needle-punching step. As such, the term "needle-punched" is understood to reference a physical state of the substrate and not a process. Likewise, the term "hydro-entangled" is understood to reference a physical state of the substrate and not a process. In other words, while hydro-entangling is a process whereby the substrate may be modified, a hydro-entangled substrate is a material that is defined at least in part by the intertwining of fibers that would not be present prior to undertaking a hydro-entangling step. In one or more implementations, a substrate as described herein can comprise a plurality of layers. For example, two or more layers having the same composition can be combined. Alternatively, two or more layers of differing compositions may be combined. It should be noted that in some implementations, a substrate sheet may comprise one or more layers of a nonwoven fibers. In still other implementations, a substrate sheet may comprise woven fabrics and/or a combination of woven and nonwoven fabrics.

In various implementations, a plurality of conductive threads are integrated into the non-woven web to create a composite substrate sheet. In some implementations, the threads may be constructed of a thermally and/or electrically conductive material, including, but not limited to, aluminum, steel (e.g., stainless steel), platinum, gold, silver, iron, brass, bronze, copper, carbon, graphite, or any combinations thereof. In various implementations, the conductive threads may be integrated into the non-woven web using a variety of different methods. For example, in one implementation the plurality of conductive threads may be integrated into the non-woven web using a stitching technique. In other implementations, the conductive threads may be integrated into the non-woven web using a tailored fiber placement (TFP) technique. See, for example, the tailored fiber placement technology platform available from Filacon Technologies of Winterlingen, Germany and LayStitch Technologies of Highland, Mich. See also U.S. Pat. No. 7,942,993 to Gessler et al. and U.S. Pat. App. Pub. No. 2010/0126652 to Joern et al., each of which is incorporated by reference in its entirety. In other implementations, the plurality of conductive threads may be integrated into the non-woven web using a stitch bonding method. It should be noted that in various implementations where stitching, lay stitching, and/or stitch bonding methods are utilized, one or more additional layers may be included to provide a multilayered composite fabric. For example, in one implementation a nonwoven, woven, or a mixture of the two may be combined with a reconstituted sheet, such as one with certain flavors, which may be combined with metal yarns/fibers prior to applying a coating slurry containing another type of flavor.

As noted, in some implementations, a composite substrate sheet may be manufactured according to a tailored fiber placement process on customary CNC-controlled automatic sewing and embroidering machines, which are also used, for example, in the textile industry. For example, during a tailored fiber placement process, one or more conductive threads may be sewed by needle and thread onto the base material (e.g., the non-woven web), which may be held in a frame, with each conductive thread (or threads) stitched to the non-woven using this sewing technique. In various implementations, the conductive threads may be laid out in a variety of directions and geometrical designs. Some example machines capable of adaption to form the products of the invention are commercially available from LayStitch Technologies. Further discussion relating to various tailored fiber placement (TFP) techniques can be found in U.S. Pat. No. 9,386,800 to Sebastian et al, which is incorporated herein by reference in its entirety.

Regardless of the method in which the conductive threads are integrated into the non-woven web, in various implementations, the pattern and/or orientation of the conductive threads may vary. FIG. 4 illustrates a schematic drawing of a non-woven web with integrated conductive threads, according to an example implementation of the present disclosure. In particular, FIG. 4 shows composite substrate sheet 120, which comprises a non-woven web 122 and a plurality of conductive threads 124 integrated therewith. Although as noted above, in various implementations, the threads may have a variety of different configurations, in the depicted implementation the conductive threads 124 are arranged in a substantially linear and parallel pattern. Further, the conductive threads 124 of the depicted implementation are substantially aligned with a longitudinal direction of the non-woven web 122, although in other implementations other orientations are possible.

In various implementations, the non-woven web and integrated conductive threads may then be coated with a coating. In some implementations, the coating may include one or more of the following ingredients: a fibrous material comprising a tobacco or a non-tobacco material, a binder material, a burn retardant, an aerosol precursor composition, and a flavorant. Although in various implementations the respective amounts of the various ingredients may vary, in one implementation the coating may include less than 10% of a binder material, less than 5% of a burn retardant material, and from at least 10% to in excess of 50% of an aerosol precursor composition. In such implementations, the amount of fibrous material and the amount of flavorant may be adjusted based on the particular application.

In some implementations, the aerosol generating component may include tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a burn retardant (e.g., diammonium phosphate and/or another salt) configured to help prevent ignition, pyrolysis, combustion, and/or scorching of the aerosol delivery component by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

In some implementations, other flame/burn retardant materials and additives may be included within the aerosol generating component and my include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the aerosol generating component and/or other components (whether alone or in combination with each other and/or other materials), the desirable properties are preferably provided without undesirable off-gassing, chemically reactive, or melting-type behavior. Additional flavorants, flavoring agents, additives, and other possible enhancing constituents are described in U.S. patent application Ser. No. 15/707,461 to Phillips et al., which is incorporated herein by reference in its entirety.

In various implementations, the fibrous material may comprise a milled tobacco material. Tobacco materials that may be useful in the present disclosure can vary and may include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT Pat. App. Pub. No. WO 02/37990 to Bereman; and Bombick et al., Fund. Appl. Toxicol., 39, p. 11-17 (1997); which are incorporated herein by reference in their entireties. Further examples of tobacco compositions that may be useful are disclosed in U.S. Pat. No. 7,726,320 to Robinson et al., which is incorporated herein by reference in its entirety. In some implementations, the milled tobacco material may comprise a blend of flavorful and aromatic tobaccos. In another implementation, the tobacco material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety.

In some implementations, the fibrous material may comprise a plant-derived non-tobacco material, including, but not limited to, hemp, flax, sisal, rice straw, esparto, and/or a cellulose pulp material. In various other implementations, the fibrous material may comprise reconstituted tobacco by itself or combined with other fibrous materials. Some example manners and methods for providing a reconstituted tobacco sheet, including casting and paper-making techniques, are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,707 to Kumar; each of which is incorporated herein by reference in its entirety. In some instances, processed tobaccos, such as certain types of reconstituted tobaccos, can be employed as longitudinally extending strands. See, for example, the type of configuration set forth in U.S. Pat. No. 5,025,814 to Raker, which is incorporated herein by reference in its entirety. In addition, certain types of reconstituted tobacco sheets can be formed, rolled, or gathered into a desired configuration. In still other implementations, the fibrous material may comprise inorganic fibers of various types (e.g., fiber glass, metal wires/screens, etc.) and/or (organic) synthetic polymers. In various implementations, these "fibrous" materials could be unstructured (e.g., randomly distributed like the cellulose fibers in tobacco cast sheet) or structured (e.g., a wire mesh).

As noted, in various implementations the coating may include a binder material, which may be in addition to, or an alternative to, any binder material included in the nonwoven. Preferred binder materials include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethylcellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass. In some other implementations, the binder may include a cyclodextrin.

As noted, the coating may also include a burn retardant material. One example of such a material is ammonium phosphate. In some implementations, other flame/burn retardant materials and additives may be included within the substrate sheet and my include organo-phosphorus compounds, borax, hydrated alumina, graphite, potassium tripolyphosphate, dipentaerythritol, pentaerythritol, and polyols. Others such as nitrogenous phosphonic acid salts, monoammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the substrate material and/or other components (whether alone or in combination with each other and/or other materials), the desirable properties are preferably provided without undesirable off-gassing or melting-type behavior. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties. Additional additives, and other possible enhancing constituents are described in U.S. patent application Ser. No. 15/707,461 to Phillips et al., which is incorporated herein by reference in its entirety.

As noted, the coating may also include an aerosol precursor composition. In some implementations, the aerosol precursor composition may comprise glycerin or propylene glycol. Preferred aerosol forming materials include polyhydric alcohols (e.g., glycerin, propylene glycol, and triethylene glycol) and/or water, and any other materials which yield a visible aerosol, as well as any combinations thereof. Representative types of aerosol forming materials are set forth in U.S. Pat. No. 4,793,365 to Sensabaugh, Jr. et al.; and U.S. Pat. No. 5,101,839 to Jakob et al.; PCT Pat. App. Pub.

No. WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference in their entirety. Other representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by British American Tobacco. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor composition, and are described, by way of example, in U.S. Pat. App. Pub. No. 2012/0055494 to Hunt et al., which is incorporated herein by reference in its entirety. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein in their entireties. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference in their entireties.

As noted, the coating may also include a flavorant. As used herein, reference to a "flavorant" refers to compounds or components that can be aerosolized and delivered to a user and which impart a sensory experience in terms of taste and/or aroma. Some examples of flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Some examples of plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As such, in various implementations a coated composite substrate sheet may be created that comprises the coated non-woven web with plurality of conductive threads integrated therewith. In various implementations, one or more composite substrate sheets may be used as a substrate portion, which may be part of an aerosol source member. FIG. 5 illustrates a perspective schematic view of an aerosol source member, according to an example implementation of the disclosure. In particular, FIG. 5 illustrates the aerosol source member 104 having a substrate portion 110 that comprises a series of overlapping layers 130 of the composite substrate sheet 120. With reference to the description above, in the depicted implementation, the composite substrate sheet 120 comprises a non-woven web a least partially formed from regenerated cellulose fibers having a multilobal cross-section and a plurality of conductive threads that are integrated into the non-woven web. In various implementations, the overlapping layers may also be considered a "gathered web." It should be noted that although the depicted implementation illustrates a relatively orderly arrangement of the layers, in various implementations, the term "overlapping layers" and "gathered web" may also include bunched, crumped, and/or otherwise gathered layers in which the individual layers may not be obvious.

In the depicted implementation, the plurality of conductive threads 124 in the series of overlapping layers 130 are oriented such that they are substantially aligned with a longitudinal axis of the substrate portion 110. However, in other implementations the plurality of conductive threads may have any orientation. For example, in some implementations, the plurality of conductive threads in the series of overlapping layers may have an orientation that is substantially perpendicular to a longitudinal axis of the substrate portion 110. In other implementations, the plurality of conductive threads in the series of overlapping layers may have an orientation that is substantially transverse, at any angle, to a longitudinal axis of the substrate portion 110. For example, in some implementations the plurality of conductive threads in the series of overlapping layers may be substantially transverse to a longitudinal axis of the substrate portion 110 at approximately a 45° angle, or at approximately a 135° angle, or at any angle less than approximately 45°, or any angle between approximately 45° and approximately 135°, or any angle greater than approximately 135°. In other implementations, the plurality of conductive threads may comprise a pattern. For example, in some implementations the plurality of conductive threads may comprise a cross pattern of conductive threads (e.g., a substantially perpendicular cross pattern or a substantially diamond shaped cross pattern). For such implementations, the cross pattern of conductive threads may have an orientation with respect to a longitudinal axis of the substrate portion 110 as similarly described above.

While in some implementations the substrate portion may merely comprise overlapping layers of the composite substrate sheet, in other implementations at least a portion of the overlapping layers may be covered with one or more cover layers. For example, FIG. 6 illustrates a schematic cross-section drawing of a substrate portion of an aerosol source member, according to an example implementation of the present disclosure. In particular, FIG. 6 illustrates the substrate portion 110, which comprises a series of overlapping layers 130 of the composite substrate sheet 120. In the depicted implementation, at least a portion of the overlapping layers 130 is substantially surrounded about its outer surface with a first cover layer 132. Although in various implementations the composition of the first cover layer 132 may vary, in the depicted implementation the first cover layer 132 comprises a combination of a fibrous material, an aerosol precursor composition, and a binder material. Reference is made to the discussions above relating possible fibrous materials, aerosol precursor compositions, and binder materials.

In various implementations, the first cover layer 132 may be constructed via a casting process, such as that described in U.S. Pat. No. 5,697,385 to Seymour et al., the disclosure of which is incorporated herein by reference in its entirety. For example, in some implementations the fibrous material, aerosol precursor composition, and binder may be blended together to form a slurry, which may be cast onto a surface (such as, for example, a moving belt). The cast slurry may then experience one or more drying and/or doctoring steps such that the result is a relatively consistent thickness cast sheet. Other examples of casting and paper-making techniques, are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,706 to Kumar; the disclosures of which is incorporated herein by reference in their entireties.

In the depicted implementation, at least a portion of the overlapping layers 130 and the first cover layer 132 are substantially surrounded about an outer surface with a second cover layer 134. Although the composition of the second cover layer 134 may vary, in the depicted implementation the second cover layer 134 comprises a metal foil material, such as an aluminum foil material. In other implementations, the second cover layer may comprise other materials, including, but not limited to, a copper material, a tin material, a gold material, a graphene material, a graphite material or other thermally conductive carbon-based material, and/or any combinations thereof. The depicted implementation further includes a third cover layer 136, which substantially surrounds the overlapping layers 130, first cover layer 132, and the second cover layer 134, about an outer surface thereof. In the depicted implementation, the third cover layer 136 comprises a paper material, such as a conventional cigarette wrapping paper. In various implementations, the paper material may comprise rag fibers, such as non-wood plant fibers, and may include flax, hemp, sisal, rice straw, and/or esparto fibers.

Although in some implementations an aerosol source member and a control body may be provided together as a complete smoking article or pharmaceutical delivery article generally, the components may be provided separately. For example, the present disclosure also encompasses a disposable unit for use with a reusable smoking article or a reusable pharmaceutical delivery article. In specific implementations, such a disposable unit (which may be an aerosol source member as illustrated in the appended figures) can comprise a substantially tubular shaped body having a heated end configured to engage the reusable smoking article or pharmaceutical delivery article, an opposing mouth end configured to allow passage of an inhalable substance to a consumer, and a wall with an outer surface and an inner surface that defines an interior space. Various implementations of an aerosol source member (or cartridge) are described in U.S. Pat. No. 9,078,473 to Worm et al., which is incorporated herein by reference in its entirety.

Although some figures described herein illustrate the control body and aerosol source member in a working relationship, it is understood that the control body and the aerosol source member may exist as individual devices. Accordingly, any discussion otherwise provided herein in relation to the components in combination also should be understood as applying to the control body and the aerosol source member as individual and separate components.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further implementations, a kit may comprise a plurality of aerosol source members. A kit may further comprise a plurality of aerosol source members and one or more batteries and/or one or more charging components. In the above implementations, the aerosol source members or the control bodies may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

FIG. 7 illustrates a perspective view of an aerosol source member, according to another example implementation of the present disclosure, and FIG. 8 illustrates a perspective view of the aerosol source member of FIG. 7 with an outer wrap removed. In particular, FIG. 7 illustrates an aerosol source member 300 that includes an outer wrap 302, and FIG. 8 illustrates the aerosol source member 300 wherein the outer wrap 302 is removed to reveal the other components of the aerosol source member 300. In the depicted implementation, the aerosol source member 300 of the depicted implementation includes a heat source 304, a substrate portion 310, an intermediate component 308, and a filter 312. In the depicted implementation, the intermediate component 308 and the filter 312 together comprise a mouthpiece 314. As will be discussed in more detail below, in various implementations the substrate portion 310 may comprise a series of overlapping layers of a composite substrate sheet that comprises a non-woven web at least partially formed from regenerated cellulose fibers.

Although an aerosol deliver device and/or an aerosol source member according to the present disclosure may take on a variety of implementations, as discussed in detail below, the use of the aerosol delivery device and/or aerosol source member by a consumer will be similar in scope. The foregoing description of use of the aerosol delivery device and/or aerosol source member is applicable to the various implementations described through minor modifications, which are apparent to the person of skill in the art in light of the further disclosure provided herein. The description of use, however, is not intended to limit the use of the articles of the present disclosure but is provided to comply with all necessary requirements of disclosure herein.

In various implementations, the heat source 304 may be configured to generate heat upon ignition thereof. In the depicted implementation, the heat source 304 comprises a combustible fuel element that has a generally cylindrical shape and that incorporates a combustible carbonaceous material. In other implementations, the heat source 304 may have a different shape, for example, a prism shape having a cubic or hexagonal cross-section. Carbonaceous materials generally have a high carbon content. Preferred carbonaceous materials may be composed predominately of carbon, and/or typically may have carbon contents of greater than about 60 percent, generally greater than about 70 percent, often greater than about 80 percent, and frequently greater than about 90 percent, on a dry weight basis.

In some instances, the heat source 304 may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite fibers; iron oxide powder; glass filaments; powdered calcium carbonate; alumina granules; ammonia sources, such as ammonia salts; and/or binding agents, such as guar gum, ammonium alginate and sodium alginate). Although specific dimensions of an applicable heat source may vary, in some implementations, the heat source 304 may have a length in an inclusive range of approximately 7 mm to approximately 20 mm, and in some implementations may be approximately 17 mm, and an overall diameter in an inclusive range of approximately 3 mm to approximately 8 mm, and in some implementations may be approximately 4.8 mm (and in some implementations, approximately 7 mm). Although in other implementations, the heat source may be constructed in a variety of ways, in the depicted implementation, the heat source 304 is extruded or compounded using a ground or powdered carbonaceous material, and has a density that is greater than about 0.5 g/cm$^3$, often greater than about 0.7 g/cm$^3$, and frequently greater than about 1 g/cm$^3$, on a dry weight basis. See, for example, the types of fuel source components, formulations and designs set forth in U.S. Pat. No. 5,551,451 to Riggs et al. and U.S. Pat. No. 7,836,897 to Borschke et al., which are incorporated herein by reference in their entireties. Although in various implementations, the heat source may have a variety of forms, including, for example, a substantially solid cylindrical shape or a hollow cylindrical (e.g., tube) shape, the heat source 304 of the depicted implementation comprises an extruded monolithic carbonaceous material that has a generally cylindrical shape but with a plurality of grooves 316 extending longitudinally from a first end of the extruded monolithic carbonaceous material to an opposing second end of the extruded monolithic carbonaceous material. In some implementations, the aerosol delivery device, and in particular, the heat source, may include a heat transfer component. In various implementations, a heat transfer component may be proximate the heat source, and, in some implementations, a heat transfer component may be located in or within the heat source. Some examples of heat transfer components are described in in U.S. patent application Ser. No. 15/923,735, filed on Mar. 16, 2018, and titled Smoking Article with Heat Transfer Component, which is incorporated herein by reference in its entirety.

Although in the depicted implementation, the grooves 316 of the heat source 304 are substantially equal in width and depth and are substantially equally distributed about a circumference of the heat source 304, other implementations may include as few as two grooves, and still other implementations may include as few as a single groove. Still other implementations may include no grooves at all. Additional implementations may include multiple grooves that may be of unequal width and/or depth, and which may be unequally spaced around a circumference of the heat source. In still other implementations, the heat source may include flutes and/or slits extending longitudinally from a first end of the extruded monolithic carbonaceous material to an opposing second end thereof. In some implementations, the heat source may comprise a foamed carbon monolith formed in a foam process of the type disclosed in U.S. Pat. No. 7,615,184 to Lobovsky, which is incorporated herein by reference in its entirety. As such, some implementations may provide advantages with regard to reduced time taken to ignite the heat source. In some other implementations, the heat source may be co-extruded with a layer of insulation (not shown), thereby reducing manufacturing time and expense. Other implementations of fuel elements include carbon fibers of the type described in U.S. Pat. No. 4,922,901 to Brooks et al. or other heat source implementations such as is disclosed in U.S. Pat. App. Pub. No. 2009/0044818 to Takeuchi et al., each of which is incorporated herein by reference in its entirety.

Generally, the heat source is positioned sufficiently near an aerosol delivery component (e.g., a substrate portion) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device elements are appreciated upon consideration of commercially available electronic aerosol delivery devices, such as those representative products listed in the background art section of the present disclosure.

Referring back to FIGS. 7 and 8, the outer wrap 302 may be provided to engage or otherwise join together at least a portion of the heat source 304 with the substrate portion 310 and at least a portion of the mouthpiece 314. In various implementations, the outer wrap 302 is configured to be retained in a wrapped position in any manner of ways including via an adhesive, or a fastener, and the like, to allow the outer wrap 302 to remain in the wrapped position. Otherwise, in some other aspects, the outer wrap 302 may be configured to be removable as desired. For example, upon retaining the outer wrap 302 in a wrapped position, the outer wrap 302 may be able to be removed from the heat source 304, the substrate portion 310, and/or the mouthpiece 314.

In some implementations, in addition to the outer wrap 302, the aerosol delivery device may also include a liner that is configured to circumscribe the substrate portion 310 and at least a portion of the heat source 304. Although in other implementations the liner may circumscribe only a portion of the length of the substrate portion 310, in some implementations, the liner may circumscribe substantially the full length of the substrate portion 310. In some implementations, the outer wrap material 302 may include the liner. As such, in some implementations the outer wrap material 302 and the liner may be separate materials that are provided together (e.g., bonded, fused, or otherwise joined together as a laminate). In other implementations, the outer wrap 302 and the liner may be the same material. In any event, the liner may be configured to thermally regulate conduction of the heat generated by the ignited heat source 304, radially outward of the liner. As such, in some implementations, the liner may be constructed of a metal foil material, a graphene material, a graphite material or other thermally conductive carbon-based material, and/or an aluminum material, and in some implementations may comprise a laminate. In some implementations, depending on the material of the outer wrap 302 and/or the liner, a thin layer of insulation may be provided radially outward of the liner. Thus, the liner may advantageously provide, in some aspects, a manner of engaging two or more separate components of the aerosol source member 300 (such as, for example, the heat source 304, the substrate portion 310, and/or a portion of the mouthpiece 314), while also providing a manner of facilitating heat transfer axially therealong, but restricting radially outward heat conduction.

As shown in FIG. 7, the outer wrap 302 (and, as necessary, the liner, and the substrate portion 310) may also include one or more openings formed therethrough that allow the entry of air upon a draw on the mouthpiece 314. In various implementations, the size and number of these openings may vary based on particular design requirements. In the depicted implementation, a plurality of openings 320 are located proximate an end of the substrate portion 310 closest to the heat source 304, and a plurality of separate cooling openings 321 are formed in the outer wrap 302 (and, in some implementations, the liner) in an area proximate the filter 312 of the mouthpiece 314. Although other implementations may differ, in the depicted implementation, the openings 320 comprise a plurality openings substantially evenly spaced about the outer surface of the aerosol source member 300, and the openings 321 also comprise a plurality of openings substantially evenly spaced around the outer surface of the aerosol source member 300. Although in various implementations the plurality of openings may be formed through the outer wrap 302 (and, in some implementations, the liner) in a variety of ways, in the depicted implementation, the plurality of openings 320 and the plurality of separate cooling openings 321 are formed via laser perforation.

In the depicted implementation, the aerosol source member 300 includes a substrate portion 310 having opposed first and second ends, wherein the first end is disposed proximate the heat source 304. Although the depicted implementation only includes one substrate portion, other implementations may include separate substrate portions, such as a second substrate portion disposed proximate the second end of substrate portion 310. In other implementations, additional substrate portions may be included. As discussed in more detail below, in various implementations the substrate portion 310 may comprise a series of overlapping layers of a composite substrate sheet.

As noted above, in various implementations the substrate portion 310 may comprise a series of overlapping layers of a composite substrate sheet that comprises a non-woven web at least partially formed from regenerated cellulose fibers. As a non-limiting example, a suitable regenerated cellulose fiber may be a viscose fiber prepared from any variety of cellulose-containing materials, such as wood (e.g., eucalyptus trees), grasses (e.g., bamboo), cotton, and other plant-based materials. In addition to the type of material used to form the fibers, substrate sheets as disclosed herein may exhibit desirable properties as least in part due to the physical structure of the fiber. It is common for fibers (particularly extruded fibers) to be solid and have a substantially round cross-section. While fibers of such construction may also be included in the present substrate sheets (e.g., as a blend), it can be particularly useful for the substrate sheets to include fibers having a multi-lobal cross-section. For example, the present substrate sheets may comprise multi-lobal fibers in an amount of about 25% or more, about 50% or more, about 60% or more, about 75% or more, about 90% or more, or about 99% or more by weight based on the total weight of fibers present in the substrate.

It should be understood that the foregoing values will have an inherent maximum of 100% by weight—e.g., wherein all fibers used in forming the substrate sheet are multi-lobal fibers. In some implementations, the multi-lobal fibers may comprise about 25% to about 100%, about 50% to about 100%, or about 90% to about 100% by weight of the substrate sheet, based on the total weight of fibers present in the substrate sheet. It should be understood that the terms "multi-lobal fiber" and "fiber having a multi-lobal cross-section" are meant to be interchangeable. In some implementations, a multi-lobal fiber can be a fiber that, in cross-section, includes a common base or hub (typically at about a central portion of the cross-section of the fiber) with at least three lobes or spokes extending therefrom. A multi-lobal fiber may further be defined as a fiber having three or more extensions such that at least one set of adjacent extensions form an angle of less than 180 degrees and thereby define one or more channels extending longitudinally along the fiber. Non-limiting examples of multi-lobal fibers are shown in FIG. 9.

As seen in FIG. 9, a multi-lobal fiber 400 includes a plurality of lobes 402 extending from a central hub 404, with adjacent lobes having an angle $\beta$ that is less than 180 degrees so as to form a channel 406 between the adjacent lobes. The lobes of a multi-lobal fiber can have a variety of shapes. For example, in some implementations the plurality of lobes may be substantially rounded while still forming a plurality of channels between adjacent lobes. In another implementation, a multi-lobal fiber may have a cross-section that is substantially elongated so as to allow for a greater number of lobes and thus a greater number of channels between the adjacent lobes. The number of lobes can vary and can be for example, 3 to 30, 3 to 20, or 3 to 10. Likewise, the spacing between lobes and the size of the lobes in the same fiber can vary. The multi-lobal fibers preferably can include surface features that can further improve the liquid handling properties thereof. As seen in FIG. 9, the plurality of lobes 402 include outer surfaces 408 that have a plurality of striations 410 that form micro- or nano-channels that can further the liquid retention and/or liquid transfer abilities of the fibers. A specific example of a multi-lobal fiber that is also striated and that can be particularly useful according to the present disclosure is fibers sold under the brand name GALAXY® from Kelheim Fibres.

A substrate sheet according to the present disclosure can be formed of a single layer of nonwoven fibers. A layer of fibers can be formed by any suitable method, such as wet-laid methods and dry-laid methods (e.g., carding or air-laid methods). Preferably, the fibers utilized in forming the substrates are staple fibers. If desired, a binder may be used, such as binders that typically may be used with cellulose esters. A binder is understood to be a material that imparts a cohesive effect to the fibers used in forming the disclosed reservoirs. For example, the binder can be a material that partially solubilizes the fibers such that the fibers bind to each other or to further fibrous materials included in the non-woven reservoir. Some examples of binders that can be used include polyvinyl acetate (PVA) binders, starch, and triacetin. In some implementations, cohesiveness may be provided through alternate means, such as through needle punching or other mechanical processes for intertwining the fibers (e.g., hydro-entanglement). A substrate sheet thus can be defined by the actual physical structure of being a needle-punched substrate in that the fibers are intertwined in a manner that would not be present prior to undertaking a needle-punching step. As such, the term "needle-punched" is understood to reference a physical state of the substrate and not a process. Likewise, the term "hydro-entangled" is understood to reference a physical state of the substrate and not a process. In other words, while hydro-entangling is a process whereby the substrate may be modified, a hydro-entangled substrate is a material that is defined at least in part by the intertwining of fibers that would not be present prior to undertaking a hydro-entangling step. In one or more implementations, a substrate as described herein can comprise a plurality of layers. For example, two or more layers having the same composition can be combined. Alternatively, two or more layers of differing compositions may be combined. It should be noted that in some implementations, a substrate sheet may comprise one or more layers of a nonwoven fibers. In still other implementations, a substrate sheet may comprise woven fabrics and/or a combination of woven and nonwoven fabrics.

In various implementations, a plurality of conductive threads are integrated into the non-woven web to create a composite substrate sheet. In some implementations, the threads may be constructed of a thermally and/or electrically conductive material, including, but not limited to, aluminum, steel (e.g., stainless steel), platinum, gold, silver, iron, brass, bronze, copper, carbon, graphite, or any combinations thereof. In various implementations, the conductive threads may be integrated into the non-woven web using a variety of different methods. For example, in one implementation the plurality of conductive threads may be integrated into the non-woven web using a stitching technique. In other implementations, the conductive threads may be integrated into the non-woven web using a tailored fiber placement (TFP) technique. See, for example, the tailored fiber placement technology platform available from Filacon Technologies of Winterlingen, Germany and LayStitch Technologies of Highland, Mich. See also U.S. Pat. No. 7,942,993 to Gessler et al. and U.S. Pat. Pub. No. 2010/0126652 to Joern et al., each of which is incorporated by reference in its entirety. In other implementations, the plurality of conductive threads may be integrated into the non-woven web using a stitch bonding method.

As noted, in some implementations, a composite substrate sheet may be manufactured according to a tailored fiber placement process on customary CNC-controlled automatic sewing and embroidering machines, which are also used, for example, in the textile industry. For example, during a tailored fiber placement process, one or more conductive threads may be sewed by needle and thread onto the base material (e.g., the non-woven web), which may be held in a frame, with each conductive thread (or threads) stitched to the non-woven using this sewing technique. In various implementations, the conductive threads may be laid out in a variety of directions and geometrical designs. Some examples of machines capable of adaption to form the products of the invention are commercially available from LayStitch Technologies. Further discussion relating to various tailored fiber placement (TFP) techniques can be found in U.S. Pat. No. 9,386,800 to Sebastian et al, which is incorporated herein by reference in its entirety.

Regardless of the method in which the conductive threads are integrated into the non-woven web, in various implementations, the pattern and/or orientation of the conductive threads may vary. FIG. 10 illustrates a schematic drawing of a non-woven web with integrated conductive threads, according to an example implementation of the present disclosure. In particular, FIG. 10 shows composite substrate sheet 320, which comprises a non-woven web 322 and a plurality of conductive threads 324 integrated therewith. Although as noted above, in various implementations, the threads may have a variety of different configurations, in the depicted implementation the conductive threads 324 are arranged in a substantially linear and parallel pattern. Further, the conductive threads 324 of the depicted implementation are substantially aligned with a longitudinal direction of the non-woven web 322, although in other implementations other orientations are possible.

In various implementations, the non-woven web and integrated conductive threads may then be coated with a coating. In some implementations, the coating may include one or more of the following ingredients: a fibrous material comprising a tobacco or a non-tobacco material, a binder material, a burn retardant, an aerosol precursor composition, and a flavorant. Although in various implementations the respective amounts of the various ingredients may vary, in one implementation the coating may include less than 10% of a binder material, less than 5% of a burn retardant material, and from at least 10% to in excess of 50% of an aerosol precursor composition. In such implementations, the amount of fibrous material and the amount of flavorant may be adjusted based on the particular application.

In some implementations, the aerosol generating component may include tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a burn retardant (e.g., diammonium phosphate and/or another salt) configured to help prevent ignition, pyrolysis, combustion, and/or scorching of the aerosol delivery component by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App.

Pub. No. 2007/0215167 to Crooks et al.; the disclosures of which are incorporated herein by reference in their entireties.

In some implementations, other flame/burn retardant materials and additives may be included within the aerosol generating component and my include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the aerosol generating component and/or other components (whether alone or in combination with each other and/or other materials), the desirable properties are preferably provided without undesirable off-gassing, chemically reactive, or melting-type behavior. Additional flavorants, flavoring agents, additives, and other possible enhancing constituents are described in U.S. patent application Ser. No. 15/707,461 to Phillips et al., which is incorporated herein by reference in its entirety.

In various implementations, the fibrous material may comprise a milled tobacco material. Tobacco materials that may be useful in the present disclosure can vary and may include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT Pat. App. Pub. No. WO 02/37990 to Bereman; and Bombick et al., Fund. Appl. Toxicol., 39, p. 11-17 (1997); which are incorporated herein by reference in their entireties. Further examples of tobacco compositions that may be useful are disclosed in U.S. Pat. No. 7,726,320 to Robinson et al., which is incorporated herein by reference in its entirety. In some implementations, the milled tobacco material may comprise a blend of flavorful and aromatic tobaccos. In another implementation, the tobacco material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety.

In some implementations, the fibrous material may comprise a plant-derived non-tobacco material, including, but not limited to, hemp, flax, sisal, rice straw, esparto, and/or a cellulose pulp material. In various other implementations, the fibrous material may comprise reconstituted tobacco by itself or combined with other fibrous materials. Some examples of manners and methods for providing a reconstituted tobacco sheet, including casting and paper-making techniques, are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,707 to Kumar; each of which is incorporated herein by reference in its entirety. In some instances, processed tobaccos, such as certain types of reconstituted tobaccos, can be employed as longitudinally extending strands. See, for example, the type of configuration set forth in U.S. Pat. No. 5,025,814 to Raker, which is incorporated herein by reference in its entirety. In addition, certain types of reconstituted tobacco sheets can be formed, rolled, or gathered into a desired configuration. In still other implementations, the fibrous material may comprise inorganic fibers of various types (e.g., fiber glass, metal wires/screens, etc.) and/or (organic) synthetic polymers. In various implementations, these "fibrous" materials could be unstructured (e.g., randomly distributed like the cellulose fibers in tobacco cast sheet) or structured (e.g., a wire mesh).

As noted, in various implementations the coating may include a binder material, which may be in addition to, or an alternative to, any binder material included in the non-woven. Preferred binder materials include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethylcellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass. In some other implementations, the binder may include a cyclodextrin.

As noted, the coating may also include a burn retardant material. One example of such a material is ammonium phosphate. In some implementations, other flame/burn retardant materials and additives may be included within the substrate sheet and may include organo-phosphorus compounds, borax, hydrated alumina, graphite, potassium tripolyphosphate, dipentaerythritol, pentaerythritol, and polyols. Others such as nitrogenous phosphonic acid salts, monoammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the substrate material and/or other components (whether alone or in combination with each other and/or other materials), the desirable properties are preferably provided without undesirable off-gassing or melting-type behavior. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties. Additional additives, and other possible enhancing constituents are described in U.S. patent application Ser. No. 15/707,461 to Phillips et al., which is incorporated herein by reference in its entirety.

As noted, the coating may also include an aerosol precursor composition. In some implementations, the aerosol precursor composition may comprise glycerin or propylene glycol. Preferred aerosol forming materials include polyhydric alcohols (e.g., glycerin, propylene glycol, and triethylene glycol) and/or water, and any other materials which yield a visible aerosol, as well as any combinations thereof. Representative types of aerosol forming materials are set forth in U.S. Pat. No. 4,793,365 to Sensabaugh, Jr. et al.; and U.S. Pat. No. 5,101,839 to Jakob et al.; PCT Pat. App. Pub. No. WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference in their entirety. Other representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by British American Tobacco. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor composition, and are described, by way of example, in U.S. Pat. App. Pub. No. 2012/0055494 to Hunt et al., which is incorporated herein by reference in its entirety. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein in their entireties. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference in their entireties.

As noted, the coating may also include a flavorant. As used herein, reference to a "flavorant" refers to compounds or components that can be aerosolized and delivered to a user and which impart a sensory experience in terms of taste and/or aroma. Some examples of flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Some examples of plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Referring back to FIG. 8, the aerosol source member 300 of the depicted implementation also includes an intermediate component 308 and at least one filter 312. It should be noted that in various implementations, the intermediate component 308 or the filter 312, individually or together, may be considered a mouthpiece 314 of the aerosol source member 300. Although in various implementations, neither the intermediate component nor the filter need be included, in the depicted implementation the intermediate component 308 comprises a substantially rigid member that is substantially inflexible along its longitudinal axis. In the depicted implementation, the intermediate component 308 comprises a hollow tube structure, and is included to add structural integrity to the aerosol source member 300 and provide for cooling the produced aerosol. In some implementations, the intermediate component 308 may be used as a container for collecting the aerosol. In various implementations, such a component may be constructed from any of a variety of materials and may include one or more adhesives. Example materials include, but are not limited to, paper, paper layers, paperboard, plastic, cardboard, and/or composite materials. In the depicted implementation, the intermediate component 308 comprises a hollow cylindrical element constructed of a paper or plastic material (such as, for example, ethyl vinyl acetate (EVA), or other polymeric materials such as poly ethylene, polyester, silicone, etc. or ceramics (e.g., silicon carbide, alumina, etc.), or other acetate fibers), and the filter comprises a packed rod or cylindrical disc constructed of a gas permeable material (such as, for example, cellulose acetate or fibers such as paper or rayon, or polyester fibers).

As noted, in some implementations the mouthpiece 314 may comprise a filter 312 configured to receive the aerosol therethrough in response to the draw applied to the mouthpiece 314. In various implementations, the filter 312 is provided, in some aspects, as a circular disc radially and/or longitudinally disposed proximate the second end of the intermediate component 308. In this manner, upon draw on the mouthpiece 314, the filter 312 receives the aerosol flowing through the intermediate component 310 of the aerosol source member 300. In some implementations, the filter 312 may comprise discrete segments. For example, some implementations may include a segment providing filtering, a segment providing draw resistance, a hollow segment providing a space for the aerosol to cool, a segment providing increased structural integrity, other filter segments, and any one or any combination of the above. In some implementations, the filter 312 may additionally or alternatively contain strands of tobacco containing material, such as described in U.S. Pat. No. 5,025,814 to Raker et al., which is incorporated herein by reference in its entirety.

In various implementations the size and shape of the intermediate component 308 and/or the filter 312 may vary, for example the length of the intermediate component 310 may be in an inclusive range of approximately 10 mm to approximately 30 mm, the dimeter of the intermediate component 310 may be in an inclusive range of approximately 3 mm to approximately 8 mm, the length of the filter 312 may be in an inclusive range of approximately 10 mm to approximately 20 mm, and the diameter of the filter 312 may be in an inclusive range of approximately 3 mm to approximately 8 mm. In the depicted implementation, the intermediate component 310 has a length of approximately 20 mm and a diameter of approximately 4.8 mm (and in some implementations, approximately 7 mm), and the filter 312 has a length of approximately 15 mm and a diameter of approximately 4.8 mm (or in some implementations, approximately 7 mm).

In addition to, or as an alternative to providing an air gap, a hollow tube structure, and/or a filter downstream from the substrate portion 310 (as discussed above), other components may exist. For example, in some implementations one or any combination of the following may be positioned downstream from the substrate portion 310: phase change materials for cooling air; flavor releasing media; ion exchange fibers capable of selective chemical adsorption; aerogel particles as filter medium; and other suitable materials. Some examples of possible phase change materials include, but are limited to, salts, such as $AgNO_3$, $AlCl_3$, $TaCl_3$, $InCl_3$, $SnCl_2$, $AlI_3$, and $TiI_4$; metals and metal alloys such as selenium, tin, indium, tin-zinc, indium-zinc, or indium-bismuth; and organic compounds such as D-mannitol, succinic acid, p-nitrobenzoic acid, hydroquinone and adipic acid. Other examples are described in U.S. Pat. No. 8,430,106 to Potter et al., which is incorporated herein by reference in its entirety.

In various implementations, ignition of the heat source 304 results in aerosolization of the aerosol precursor composition associated with the substrate portion 310. Preferably, the elements of the substrate portion 310 do not experience thermal decomposition (e.g., charring, scorching, or burning) to any significant degree, and the aerosolized components are entrained in the air that is drawn through the aerosol source member 300, including the filter 312, and into the mouth of the user. In various implementations, the mouthpiece 314 (e.g., the intermediate component 308 and/or the filter 312) is configured to receive the generated aerosol therethrough in response to a draw applied to the mouthpiece 314 by a user. In some implementations, the mouthpiece 314 may be fixedly engaged to the substrate portion 310. For example, an adhesive, a bond, a weld, and the like may be suitable for fixedly engaging the mouthpiece 314 to the substrate material 310. In one example, the mouthpiece 314 is ultrasonically welded and sealed to an end of the substrate portion 310.

In various implementations a coated composite substrate sheet may be created that comprises the coated non-woven web with plurality of conductive threads integrated therewith. In various implementations, one or more composite substrate sheets may be used as a substrate portion, which may be part of an aerosol source member. FIG. 11 illustrates a perspective schematic view of a substrate portion of an aerosol delivery device, according to an example implementation of the disclosure. In particular, FIG. 11 illustrates substrate portion 310 that comprises a series of overlapping layers 330 of the composite substrate sheet 320. With reference to the description above, in the depicted implementation, the composite substrate sheet 320 comprises a non-woven web a least partially formed from regenerated cellulose fibers having a multi-lobal cross-section and a plurality of conductive threads that are integrated into the non-woven web. In various implementations, the overlapping layers may also be considered a "gathered web." It should be noted that although the depicted implementation illustrates a relatively orderly arrangement of the layers, in various implementations, the term "overlapping layers" and "gathered web" may also include bunched, crumped, and/or otherwise gathered layers in which the individual layers may not be obvious.

In the depicted implementation, the plurality of conductive threads 324 in the series of overlapping layers 330 are oriented such that they are substantially aligned with a longitudinal axis of the substrate portion 310. However, in other implementations the plurality of conductive threads may have any orientation. For example, in some implementations, the plurality of conductive threads in the series of overlapping layers may have an orientation that is substantially perpendicular to a longitudinal axis of the substrate portion 310. In other implementations, the plurality of conductive threads in the series of overlapping layers may have an orientation that is substantially transverse, at any angle, to a longitudinal axis of the substrate portion 310. For example, in some implementations the plurality of conductive threads in the series of overlapping layers may be substantially transverse to a longitudinal axis of the substrate portion 310 at approximately a 45° angle, or at approximately a 135° angle, or at any angle less than approximately 45°, or any angle between approximately 45° and approximately 135°, or any angle greater than approximately 135°. In other implementations, the plurality of conductive threads may comprise a pattern. For example, in some implementations the plurality of conductive threads may comprise a cross pattern of conductive threads (e.g., a substantially perpendicular cross pattern or a substantially diamond shaped cross pattern). For such implementations, the cross pattern of conductive threads may have an orientation with respect to a longitudinal axis of the substrate portion 310 as similarly described above.

While in some implementations the substrate portion may merely comprise overlapping layers of the composite substrate sheet, in other implementations at least a portion of the overlapping layers may be covered with one or more cover layers. For example, FIG. 12 illustrates a schematic cross-section drawing of a substrate portion of an aerosol delivery device, according to an example implementation of the present disclosure. In particular, FIG. 12 illustrates the substrate portion 310, which comprises a series of overlapping layers 330 of the composite substrate sheet 320. In the depicted implementation, at least a portion of the overlapping layers 330 is substantially surrounded about its outer surface with a first cover layer 332. Although in various implementations the composition of the first cover layer 332 may vary, in the depicted implementation the first cover layer 332 comprises a combination of a fibrous material, an aerosol precursor composition, and a binder material. Reference is made to the discussions above relating possible fibrous materials, aerosol precursor compositions, and binder materials.

In various implementations, the first cover layer 332 may be constructed via a casting process, such as that described in U.S. Pat. No. 5,697,385 to Seymour et al., the disclosure of which is incorporated herein by reference in its entirety. For example, in some implementations the fibrous material, aerosol precursor composition, and binder may be blended together to form a slurry, which may be cast onto a surface (such as, for example, a moving belt). The cast slurry may then experience one or more drying and/or doctoring steps such that the result is a relatively consistent thickness cast sheet. Other examples of casting and paper-making techniques, are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,706 to Kumar; the disclosures of which is incorporated herein by reference in their entireties.

In the depicted implementation, at least a portion of the overlapping layers 330 and the first cover layer 332 are substantially surrounded about an outer surface with a second cover layer 334. Although the composition of the second cover layer 334 may vary, in the depicted implementation the second cover layer 334 comprises a metal foil material, such as an aluminum foil material. In other implementations, the second cover layer may comprise other materials, including, but not limited to, a copper material, a tin material, a gold material, a graphene material, a graphite material or other thermally conductive carbon-based material, and/or any combinations thereof. The depicted implementation further includes a third cover layer 336, which substantially surrounds the overlapping layers 330, first cover layer 332, and the second cover layer 334, about an outer surface thereof. In the depicted implementation, the third cover 336 layer comprises a paper material, such as a conventional cigarette wrapping paper. In various implementations, the paper material may comprise rag fibers, such as non-wood plant fibers, and may include flax, hemp, sisal, rice straw, and/or esparto fibers.

FIG. 13 illustrates various operations in a method 500 of creating a substrate portion for use in an aerosol delivery device. In various implementations, the method 500 may comprise creating a composite substrate sheet by forming a non-woven web using regenerated cellulose fibers at operation 502. In one implementation this may be accomplished by forming a non-woven web using regenerated cellulose fibers at operation 504, integrating a plurality of conductive threads into the non-woven web at operation 506, and coating the non-woven web and integrated conductive threads with a coating that includes a fibrous material and an aerosol precursor composition at operation 508. The method 500 may further comprise overlapping a plurality of layers of the composite substrate sheet to create a series of overlapping layers of the composite substrate sheet at operation 510. In various implementations, further reference is made to the composite substrate sheets, regenerated cellulose fibers, conductive threads, coatings, and related methods described above with respect to FIGS. 1-12.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A substrate portion for use in an aerosol source member, said substrate portion comprising:
 a series of overlapping layers of a composite substrate sheet, the composite substrate sheet comprising:
  a non-woven web at least partially formed from regenerated cellulose fibers;
  a plurality of conductive threads integrated into the non-woven web; and
  a coating that includes a fibrous material and an aerosol precursor composition,
 wherein the plurality of conductive threads are first arranged linearly and parallel, wherein the plurality of conductive threads is substantially aligned with a longitudinal direction of the non-woven web, and wherein the composite substrate sheet is subsequently overlapped into the series of overlapping layers.

2. The substrate portion of claim 1, wherein the regenerated cellulose fibers have a multi-lobal cross-section.

3. The substrate portion of claim 1, wherein the fibrous material comprises a milled tobacco material.

4. The substrate portion of claim 1, wherein the coating further includes one or more of a binder material, a burn retardant material, and a flavorant.

5. The substrate portion of claim 1, wherein the non-woven web is configured to contain the aerosol precursor composition in a loading in excess of 40%.

6. The substrate portion of claim 1, wherein the non-woven web is configured to contain the aerosol precursor composition in a loading from at least 10% to in excess of 50%.

7. The substrate portion of claim 1, wherein the plurality of conductive threads are constructed of one or more of an aluminum material, a stainless steel material, a copper material, a carbon material, and a graphite material.

8. The substrate portion of claim 1, wherein the plurality of conductive threads are integrated into non-woven web via stitching.

9. The substrate portion of claim 1, wherein the plurality of conductive threads are integrated into non-woven web via tailored fiber placement (TFP).

10. The substrate portion of claim 1, wherein the composite substrate sheet comprises two or more layers stitch bonded together.

11. The substrate portion of claim 1, wherein the series of overlapping layers of the composite substrate sheet is wrapped on its outside with a cover layer.

12. The substrate portion of claim 11, wherein the cover layer comprises a cast sheet.

13. The substrate portion of claim 11, wherein the cover layer comprises a non-woven web at least partially formed from regenerated cellulose fibers.

14. The substrate portion of claim 11, wherein the series of overlapping layers of the composite substrate sheet and the cover layer are wrapped on the outside thereof with a second cover layer comprising a metal foil.

15. The substrate portion of claim 14, wherein the series of overlapping layers of the composite substrate sheet, the cover layer, and the second cover layer are wrapped on the outside thereof with a third cover layer comprising a paper material.

16. The substrate portion of claim 1, further comprising a binder material, an aerosol precursor composition, and a burn retardant material.

17. An aerosol source member, said aerosol source member comprising:
a substrate portion comprising:
a series of overlapping layers of a composite substrate sheet, the composite substrate sheet comprising:
a non-woven web at least partially formed from regenerated cellulose fibers;
a plurality of conductive threads integrated into the non-woven web; and
a coating that includes a fibrous material and an aerosol precursor composition,
wherein the substrate portion is formed in a substantially cylindrical shape; and
a cover layer is disposed proximate an outside surface of the substrate portion,
wherein the plurality of conductive threads are first arranged linearly and parallel, wherein the plurality of conductive threads is substantially aligned with a longitudinal direction of the non-woven web, and wherein the composite substrate sheet is subsequently overlapped into the series of overlapping layers.

18. The aerosol source member of claim 17, wherein the regenerated cellulose fibers of the substrate portion have a multi-lobal cross-section.

19. The aerosol source member of claim 17, wherein the fibrous material of the substrate portion comprises a milled tobacco material.

20. The aerosol source member of claim 17, wherein the coating of the substrate portion further includes one or more of a binder material, a burn retardant material, and a flavorant.

21. The aerosol source member of claim 17, wherein the cover layer comprises a cast sheet.

22. The aerosol source member of claim 17, wherein the cover layer comprises a non-woven web at least partially formed from regenerated cellulose fibers.

23. The aerosol source member of claim 17, further comprising a second cover layer disposed proximate an outer surface of the cover layer, the second cover layer comprising a metal foil.

24. The aerosol source member of claim 23, further comprising a third cover layer disposed proximate an outer surface of the second cover layer, wherein the third cover layer comprises a paper material.

25. The aerosol source member of claim 17, wherein the non-woven web of the substrate portion is configured to contain the aerosol precursor composition at a loading in excess of 40%.

26. The aerosol source member of claim 17, wherein the non-woven web of the substrate portion is configured to contain the aerosol precursor composition in a loading from at least 10% to in excess of 50%.

27. The aerosol source member of claim 17, wherein the plurality of conductive threads of the substrate portion are constructed of one or more of an aluminum material, a stainless steel material, a copper material, a carbon material, a graphite material.

28. The aerosol source member of claim 17, wherein the plurality of conductive threads of the substrate portion are integrated into non-woven web via stitching.

29. The aerosol source member of claim 17, wherein the plurality of conductive threads of the substrate portion are integrated into non-woven web via tailored fiber placement (TFP).

30. The aerosol source member of claim 17, wherein the composite substrate sheet comprises two or more layers stitch bonded together.

31. A method of creating a substrate portion for use in an aerosol source member, said method comprising:
first creating a composite substrate sheet by:
forming a non-woven web using regenerated cellulose fibers;
integrating a plurality of conductive threads into the non-woven web; and
coating the non-woven web and integrated conductive threads with a coating that includes a fibrous material and an aerosol precursor composition; and
subsequently overlapping a plurality of layers of the composite substrate sheet to create a series of overlapping layers of the composite substrate sheet,
wherein the step of integrating the plurality of conductive threads into the non-woven web comprises integrating the plurality of conductive threads so that they are arranged in linearly and parallel, wherein the plurality of conductive threads is substantially aligned with a longitudinal direction of the non-woven web.

32. The method of claim 31, wherein the regenerated cellulose fibers have a multi-lobal cross-section.

33. The method of claim 31, wherein the fibrous material comprises a milled tobacco material.

34. The method of claim 31, wherein the coating further includes one or more of a binder material, a burn retardant material, and a flavorant.

35. The substrate portion of claim 31, wherein the non-woven web is configured to contain the aerosol precursor composition in a loading in excess of 40%.

36. The method of claim 31, wherein the non-woven web is configured to contain the aerosol precursor composition in a loading from at least 10% to in excess of 50%.

37. The method of claim 31, wherein the plurality of conductive threads are constructed of one or more of an aluminum material, a stainless steel material, a copper material, a carbon material, and a graphite material.

38. The method of claim 31, wherein the step of integrating the plurality of conductive threads into the non-woven web comprises stitching the plurality of conductive threads into the non-woven web.

39. The method of claim 31, wherein the step of integrating the plurality of conductive threads into the non-woven web comprises tailored fiber placement (TFP).

40. The method of claim 31, wherein the composite substrate sheet comprises two or more layers stitch bonded together.

41. The method of claim 31, further comprising wrapping the series of overlapping layers of the composite substrate sheet about an outer surface thereof with a cover layer.

42. The method of claim 41, wherein the cover layer comprises a cast sheet.

43. The method of claim 41, wherein the cover layer comprises a non-woven web at least partially formed from regenerated cellulose fibers.

44. The method of claim 41, further comprising wrapping the series of overlapping layers of the composite substrate sheet and the cover layer about an outer surface thereof with a second cover layer comprising a metal foil.

45. The method of claim 44, further comprising wrapping the series of overlapping layers of the composite substrate sheet, the cover layer, and the second cover layer about an outer surface thereof with a third cover layer comprising a paper material.

* * * * *

UNITED STATES PATENT AND TRADEMARK OFFICE
CERTIFICATE OF CORRECTION

PATENT NO. : 11,753,750 B2
APPLICATION NO. : 16/196958
DATED : September 12, 2023
INVENTOR(S) : Andries D. Sebastian et al.

It is certified that error appears in the above-identified patent and that said Letters Patent is hereby corrected as shown below:

On the Title Page

In item (56), in Column 2, under "Other Publications", Line 1, delete "Trilobl" and insert -- Trilobal --.

In the Claims

In Column 40, Line 58, in Claim 31, after "arranged" delete "in".

Signed and Sealed this
Thirtieth Day of April, 2024

Katherine Kelly Vidal
*Director of the United States Patent and Trademark Office*